US009265603B2

(12) United States Patent
Sanger et al.

(10) Patent No.: US 9,265,603 B2
(45) Date of Patent: *Feb. 23, 2016

(54) INTRAOCULAR LENS

(71) Applicant: Hoya Corporation, Tokyo (JP)

(72) Inventors: Demas Sanger, Fukaya (JP); Tjundewo Lawu, Toda (JP)

(73) Assignee: Hoya Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/173,507

(22) Filed: Feb. 5, 2014

(65) Prior Publication Data

US 2014/0309736 A1 Oct. 16, 2014

Related U.S. Application Data

(63) Continuation of application No. 12/304,651, filed as application No. PCT/JP2007/061092 on May 31, 2007, now Pat. No. 8,647,383.

(30) Foreign Application Priority Data

Jun. 14, 2006 (JP) .................................. 2006-165278

(51) Int. Cl.
A61F 2/16 (2006.01)

(52) U.S. Cl.
CPC ............... *A61F 2/1624* (2013.01); *A61F 2/164* (2015.04); *A61F 2/1613* (2013.01); *A61F 2/1618* (2013.01)

(58) Field of Classification Search
USPC ....................... 623/6.27–6.29, 6.37
See application file for complete search history.

(56) References Cited

U.S. PATENT DOCUMENTS

| 4,504,982 A | 3/1985 | Burk |
| 4,778,462 A | 10/1988 | Grendahl |
| 4,795,462 A | 1/1989 | Grendahl |
| 4,813,955 A | 3/1989 | Achatz |

(Continued)

FOREIGN PATENT DOCUMENTS

| JP | 60-085744 A | 5/1985 |
| JP | 05-021922 | 3/1993 |

(Continued)

OTHER PUBLICATIONS

PCT International Search Report dated Jun. 26, 2007 for PCT App. Ser. No. PCT/JP2007/016092.

*Primary Examiner* — David H Willse
*Assistant Examiner* — Tiffany Shipmon
(74) *Attorney, Agent, or Firm* — Henricks, Slavin & Holmes LLP

(57) ABSTRACT

An intraocular lens in which deterioration in contrast is suppressed even when the optical axis of the intraocular lens is decentered from the optical axis of the eyeball when the intraocular lens is inserted into the eye while the advantage of a conventional aberration reduction type intraocular lens that the image is seen clearly is sustained by employing such a power distribution as respectively having at least one positive power deviation region (E1) having a power larger than that represented by the reference power distribution and at least one negative power deviation region (E2) having a power smaller than that represented by the reference power distribution in the central region of the intraocular lens assuming that a power distribution being set to cancel the spherical aberration of cornea when the intraocular lens is inserted into the eye is the reference power distribution.

13 Claims, 19 Drawing Sheets

(56) References Cited

U.S. PATENT DOCUMENTS

| | | | |
|---|---|---|---|
| 5,225,858 A * | 7/1993 | Portney | 351/159.42 |
| 6,015,435 A | 1/2000 | Valunin et al. | |
| 6,145,987 A | 11/2000 | Baude et al. | |
| 6,457,826 B1 | 10/2002 | Lett | |
| 8,647,383 B2 | 2/2014 | Sanger et al. | |
| 2002/0044255 A1 | 4/2002 | Ye | |
| 2004/0106992 A1* | 6/2004 | Lang et al. | 623/6.28 |
| 2004/0167623 A1 | 8/2004 | Peyman | |

FOREIGN PATENT DOCUMENTS

| | | |
|---|---|---|
| JP | 11-242193 A | 9/1999 |
| JP | 2000-509289 A | 7/2000 |
| JP | 2006-14818 | 1/2006 |
| WO | WO 97/26843 A1 | 7/1997 |
| WO | WO 97/44698 | 11/1997 |
| WO | WO 01/89424 | 11/2001 |
| WO | WO 2005/046527 A2 | 5/2005 |

\* cited by examiner

| | RADIUS OF CURVATURE (mm) | | CONIC CONSTANT | | SURFACE SEPARATION (mm) | | REFRACTIVE INDEX | |
|---|---|---|---|---|---|---|---|---|
| - | - | - | - | - | - | - | n1 | 1.0 |
| ANTERIOR SURFACE OF CORNEA | R1 | 7.8 | k | -0.25 | d1 | 0.55 | n2 | 1.3771 |
| POSTERIOR SURFACE OF CORNEA | R2 | 6.5 | - | - | d2 | 4.1 | n3 | 1.336 |
| APERTURE | - | - | - | - | a | 4.0 | - | - |
| ANTERIOR SURFACE OF INTRAOCULAR LENS | - | - | - | - | d3 | 0.7 | n4 | 1.517 |
| POSTERIOR SURFACE OF INTRAOCULAR LENS | BC | 30.0 | - | - | - | - | n5 | 1.336 |

EXPLANATORY DIAGRAM OF MODES OF REFERENCE POWER DISTRIBUTIONS

DIAGRAM SHOWING MODES OF
PATTERNS FOR ADJUSTING
POWER DISTRIBUTION

INTRAOCULAR LENS

CROSS REFERENCE TO RELATED APPLICATIONS

This application is a continuation of U.S. application Ser. No. 12/304,651, which has a 35 U.S.C. §371(c) date of Mar. 9, 2009, now U.S. Pat. No. 8,647,383, which is a U.S. national phase application under 35 U.S.C. §371 of International Patent Application No. PCT/JP2007/061092 filed May 31, 2007, which claims priority to Japanese patent application No. 2006-165278, filed Jun. 14, 2006. The International Application was published in Japanese on Dec. 21, 2007 as International Publication No. WO 2007/145082 A1. The content of each application is incorporated herein in its entirety.

TECHNICAL FIELD

The present invention relates to an intraocular lens which enables suppressing contrast deterioration due to an optic decentration which occurs when the intraocular lens is inserted into an eye.

BACKGROUND

An intraocular lens is inserted, for vision correction, into an eyeball after removing the crystalline lens due to cataract or the like. A spherical design is the mainstream of the current optical designs for an intraocular lens, because the design has many functions required for an intraocular lens moderately, is easy to manufacture, and is convenient for managing powers. However, an intraocular lens is also being developed with attention being paid to a specific function and with an aim for enhancing the function. The technological trends for enhancement of such specific function can be classified into two types. The first trend is directed to enable an eye to see both near objects and distance objects. The second trend is directed to enable an eye to see an object more clearly.

A typical intraocular lens of the first trend as described above is a multifocal intraocular lens, in which the optical region of the intraocular lens is divided into a plurality of zones, with each zone having a power distribution for seeing near objects, a power distribution for seeing intermediate objects, and a power distribution for seeing distance objects, respectively. The optical designs thereof differ depending on which distance priority is given to. In any of the designs, however, the quantity of light which enters each zone is smaller compared with a case of a spherical lens which captures light with the entire lens. As a result, despite an increased visible range, contrast of such lens is deteriorated (for example, see Patent Document 1).

An invention described in Patent Document 2 is based on a similar technological concept. Although the invention does not cover all of near, intermediate, and distance, it is directed to provide a wider visible range compared with a spherical lens, for example, with an enhanced depth of focus for near vision. Needless to say, an intraocular lens according to the invention results in a deteriorated contrast compared with a spherical lens.

On the other hand, a technology of the second trend is based on the concept which is dramatically opposite to the concept of the first trend. That is, the technology is directed to improve contrast, while sacrificing the size of the visible range. When a spherical intraocular lens is inserted into an eye, focal points are not concentrated on the retina because the aberration of the cornea itself and the aberration of the intraocular lens are overlapped with each other. The second trend is directed to reduce the aberration. The spherical aberrations of the cornea and of the intraocular lens increase, with increasing radial distance from the optical axis. That is, although influence due to the spherical aberration is little if a width of a light ray entering the eye is small, it is significant if the width of the light ray is large. For example, a driver has a pupil diameter equal to or greater than 3.2 mm when s/he drives a car at night. Such pupil diameter is greatly affected by the spherical aberration such that the contrast of an object is deteriorated, which may be dangerous for driving a car. A technology of the second trend is directed to solve this kind of problem (for example, see Patent Documents 3, 4 and 5).

All technologies disclosed in Patent Documents 3 to 5 are directed to reduce the spherical aberration. However, they have an disadvantage that they provide a smaller visible range compared with the spherical lens due to smaller depth of focus. These aberration correction lenses are directed to reduce the spherical aberration which would otherwise increase with increasing radial distance from the optical axis. Accordingly, these lenses have simpler power distributions compared with a multifocal lens.

[Patent Document 1] Japanese Patent Application Laid Open No. S60-85744

[Patent Document 2] Published Japanese Translation of a PCT Application No. 2000-511439

[Patent Document 3] U.S. Pat. No. 4,504,982

[Patent Document 4] Published Japanese Translation of a PCT Application No. 2003-534565

[Patent Document 5] Japanese Patent Application Laid Open No. 2006-14818

DISCLOSURE OF THE INVENTION

Problem to be Solved by the Invention

In the meantime, the intraocular lens for aberration reduction of the above-described second trend is found to have a major disadvantage other the small visible range as described above. That is, when an intraocular lens is placed into an eye, the optical axis of the intraocular lens is not always aligned with the optical axis of the eyeball. Instead, optic decentration is common, and it is found in literatures that an optic decentration of 0.3 mm in average is generated. FIG. 33 is a diagram showing that the optical axis of the intraocular lens is decentred from the optical axis of the eyeball. As shown in FIG. 33, when assuming the optical axis of an eyeball optical system including a cornea 20, a retina 30 and the like, is $O_I$, an optical axis $O_L$ of an intraocular lens 10 placed in the eye is decentred from $O_I$ by the amount $\Delta IL$. It is reported in literatures, textbooks, and the like, that in the case where the pupil diameter is large, deterioration in contrast in the aberration reduction type intraocular lens caused by an optic decentration is much greater compared with that in a spherical lens.

An object of the invention of the present application is to obtain an intraocular lens in which deterioration in contrast is suppressed even when the optical axis of an intraocular lens is decentred from the optical axis of an eyeball when the intraocular lens is inserted into the eye, while the advantage of a conventional aberration reduction type intraocular lens that the image is seen clearly.

Means for Solving Problems

As means for solving the above-described problem, the first means is:

an intraocular lens in which deterioration in contrast is suppressed when an optical axis of the intraocular lens inserted into an eye is decentred from an optical axis of an eyeball, by employing such a power distribution as respectively having at least one positive power deviation region having a larger power than that represented by the reference power distribution and at least one negative power deviation region having a smaller power than that represented by the reference power distribution in a region in the vicinity of the center of the intraocular lens, assuming that the reference power distribution being set to cancel a spherical aberration of cornea when an intraocular lens is inserted into the eye.

The second means is:

the intraocular lens related to the first means, wherein each of the positive power deviation region and the negative power deviation region is a circular region or an annular region centering around an optical axis.

The third means is:

the intraocular lens related to the first or second means, wherein the central region has a substantially circular shape centering around the optical axis having a radius not less than 0.7 mm and not more than 1.75 mm.

The fourth means is:

the intraocular lens according to any one of the first to third means, wherein a mean value of power deviation amounts from a reference power of the positive power deviation region is not less than 0.1 diopter and not more than 0.8 diopter, and a mean value of power deviation amounts from of a reference power of the negative power deviation region is not less than 0.1 diopter and not more than 0.8 diopter.

Effect of the Invention

According to the above-described means, it is possible to obtain an intraocular lens in which deterioration in contrast is suppressed even when the optical axis of the intraocular lens is decentred from the optical axis of the eyeball when the intraocular lens is inserted into the eye, by employing such a power distribution as respectively having at least one positive power deviation region having a larger power than that represented by the reference power distribution and one negative power deviation region having a smaller power than that represented by the reference power distribution in the central region of the intraocular lens. In this case, it is preferable that the central region have a substantially circular shape centering around the optical axis having a radius not less than 0.7 mm and not more than 1.75 mm. If the radius is smaller than 0.7 mm or larger than 1.75 mm, the function for suppressing deterioration in contrast caused by an optic decentration is not sufficient. More preferably, the radius should be within a range not less than 1.2 mm and not more than 1.5 mm. Further, it is preferable that the power deviation amounts from the reference power of the positive power deviation region or the mean value thereof be not less than 0.1 diopter and not more than 0.8 diopter, and the power deviation amounts from the reference power of the negative power deviation region or the mean value thereof be not less than 0.1 diopter and not more than 0.8 diopter. If the radius is smaller than 0.1 diopter, the function for suppressing deterioration in contrast caused by an optic decentration is not sufficient, and if the radius is larger than 0.8 diopter, a clear image cannot be obtained. With general environmental illumination being taken into consideration, more preferably, the radius should be within in a range not less than 0.2 diopter and not more than 0.5 diopter. Notably, it is found that deterioration in contrast is suppressed also when the intraocular lens is tilted when it is inserted into the eye, as well as when there is an optic decentration.

BEST MODE FOR CARRYING OUT THE INVENTION

FIG. 1 is an explanatory view of a power distribution of an intraocular lens according to an Embodiment 1 of the present invention; FIG. 2 is a schematic explanatory view of an optical system in the eye constituted by the intraocular lens and cornea, and FIG. 3 is a graph showing the power distribution of the intraocular lens according to the Embodiment 1 of the present invention, the power distribution of the spherical intraocular lens, and the reference power distribution. The intraocular lens according to the Embodiment 1 of the present invention will now be explained with reference to these drawings.

In these drawings, Numeral 10 denotes an intraocular lens (IOL). The intraocular lens 10 is a lens having a substantially-circular shape made of a soft material, such as soft acryl, silicon, hydro gel or the like, or a hard material such as PMMA. Notably, although not shown, haptics or the like are attached to an outer peripheral portion thereof, as necessary. A region 11 exists in the vicinity of an optical center O of the intraocular lens 10, that is, the region 11 is included in a circle ng around the optical center O with a radius r2. The region 11 has a region E1 included in a circle with a radius r1 which is smaller than r2, and a region E2 surrounded by the circle having the radius r1 and the circle having the radius r2 outside thereof. Further, a region E3 is defined by the outer periphery of the circle with the radius r2 and the outer circumferential edge of the lens.

In FIG. 1, the graph below the intraocular lens 10 shows the power distribution in the radial direction of the intraocular lens, while the horizontal axis represents a distance r in the radial direction from the optical center O of the intraocular lens 10, and the vertical axis represents a power P(r) of the intraocular lens 10 at each position at the distance r. In this graph, a curve $Mam_1$ shown by the solid line is the curve representing the power distribution of the intraocular lens 10 according to the present Embodiment 1. Meanwhile, the curve Ma shown by the dotted line is a reference power distribution curve representing a power distribution Ma. The power distribution Ma, serving as the reference power distribution, is set so as to cancel a spherical aberration of the cornea when the intraocular lens is inserted into the eye. The reference power distribution curve represents a power distribution which has been set so as to cancel a theoretically-assumed spherical aberration of the cornea in a theoretically perfect manner.

That is, when the intraocular lens 10 is inserted into the eye, the lens constitutes the optical system shown in FIG. 2. In this optical system, a cornea 20 has a certain type of lens function and has a spherical aberration. Then, if the intraocular lens 10 has a power distribution which cancels the spherical aberration of the cornea 20, the spherical aberration as the entire eyeball can be substantially perfectly eliminated. In this embodiment, values such as a radius of curvature, a refractive index, and the like, of the intraocular optical system including the intraocular lens 10 and the cornea 20 are set to the values shown in the table at the bottom of FIG. 2. Further, the cornea model is assumed by inputting a conic constant to the cornea anterior surface to the LeGrand eye model, which is the basis, such that the cornea model is close to the shape of a cornea of a human eye. Further, the aperture is set to be 4 mm assuming a mesopic condition when an analysis to be described later or the like is made or the like.

As shown in the table in FIG. 2, the set values are as follows: a radius of curvature R1 of the anterior surface of the cornea 20: 7.8 mm, a radius of curvature R2 of the posterior surface thereof: 6.5 mm, a thickness d1 at the central portion of the cornea: 0.55 mm; a distance d2 from the posterior surface of the cornea to the anterior surface of the intraocular lens 10: 4.1 mm, a thickness d3 at the central portion of the intraocular lens 0.7 mm; a refractive index n1 in a region which is in contact with the front surface of the cornea 20 and which is outside of the cornea: 1.0, a refractive index n2 of the cornea 20: 1.3771, the refractive index n3 in a region between the cornea 20 and the intraocular lens 10: 1.336, a refractive index n4 of the intraocular lens 10: 1.517, and a refractive index n5 in a region between the intraocular lens 10 and a field or retina (not shown): 1.336. Meanwhile, a lens having the dioptric power of 20 diopters is used as the intraocular lens according to the Embodiment 1 and the Embodiment 2 to be described later. The refractive error of the optical system (the model eye and the intraocular lens) is set to −0.75 D. In other words, myopia of −0.75 D is produced in the optical system consisting of the model eye and the intraocular lens, because myopia of from −0.5 D to −1.0 D is commonly produced in the case of a single focus intraocular lens in cataract surgery. Further, the position of the field of the optical system consisting of the model eye and the intraocular lens is set to the best focus position when the aperture of the optical system is 3 mm.

As shown in FIG. 1, with respect to the reference power distribution curve Ma, the power distribution of the intraocular lens 10 according to this embodiment is such that: a power is larger than that represented by the reference power distribution in the region E1 inside the region 11 in the vicinity of the center of the intraocular lens 20, and the region E1 serves as the positive power deviation region; and a power is smaller than that represented by the reference power distribution the in region E2 inside the region 11 in the vicinity of the center of the intraocular lens 20, and the region E2 serves as the negative power deviation region. The following equation is obtained by polynomial approximation of the power distribution of the intraocular lens according to the Embodiment 1.

$$P(r) = a_0 + a_1 r^2 + a_2 r^4 + \ldots + a_{n-1} r^{2(n-1)} + a_n r^{2n} \quad \text{Eq. 1}$$

n=8

| i | $a_i$ |
|---|---|
| 0 | 20.31296977 |
| 1 | −1.45875259 |
| 2 | 0.76120703 |
| 3 | 0.03291369 |
| 4 | −0.15203333 |
| 5 | 0.05260424 |
| 6 | −0.00812956 |
| 7 | 0.00060675 |
| 8 | −0.00001778 |

As shown in FIG. 3, the power distribution curve of the intraocular lens according to the Embodiment 1 ($Mam_1$: the curve shown by the dashed-dotted line in FIG. 3) is a curve deviating from the reference power distribution curve (Ma: the curve shown by the dotted line in FIG. 3) as if it is meandering. Meanwhile, the power distribution curve of a conventional spherical intraocular lens is shown by the solid line. The reference power distribution curve Ma represents the power distribution obtained by adding an aberration correction so as to cancel the spherical aberration which occurs in the cornea to the power distribution of a conventional spherical intraocular lens. Further, the power distribution curve $Mam_1$ of the intraocular lens according to the Embodiment 1 is a curve which is deviating from the reference power distribution curve Ma, as if it is meandering. In this case, the amount of deviation to the positive power in the region $E_1$ is +0.2 diopter in average, and the amount of deviation to the negative power in the region $E_2$ is −0.2 diopter in average.

FIG. 4 is a graph showing the spherical aberrations of the entire eyeball in the cases where the intraocular lens according to the Embodiment 1 of the present invention having the power distribution shown in FIG. 3, the spherical intraocular lens, and the intraocular lens employing the reference power distribution Ma are respectively placed in an eye. In FIG. 4, the curve shown by the solid line is the aberration distribution curve when the spherical intraocular lens is placed, the curve shown by the dotted line in the diagram is the aberration distribution curve when the intraocular lens employing the reference power distribution Ma (intraocular lens employing Ma) is placed, and the curve shown by the dashed-dotted line in the diagram is the aberration distribution curve when the intraocular lens according to the Embodiment 1 (intraocular lens of $Mam_1$) is placed.

As shown in FIG. 4, it can be seen that in the case where the spherical intraocular lens for which no correction has been made on the aberration of the cornea is placed, the aberration of the entire eyeball increases, with increasing distance away from the center of the intraocular lens. On the contrary, in the case of the intraocular lens employing the reference power distribution, the aberration of the cornea is perfectly corrected, and thus the aberration is perfectly reduced to zero. Further, in the intraocular lens according to the present embodiment, a positive aberration first occurs and subsequently a negative aberration occurs in the vicinity of the optical center. However, the aberration is reduced to zero in a region outside of such central region and closer to the outer periphery of the lens.

FIG. 5 is a graph showing the contrasts when the spatial frequency f is 50 lines/mm, in the cases where the intraocular lens according to the embodiment of the present invention, the spherical intraocular lens, and the intraocular lens employing the reference power distribution Ma are respectively placed, with each optical axis thereof being aligned with the optical axis of the intraocular optical system. In the graph of FIG. 5, the vertical axis represents the contrast, and the horizontal axis represents the distance from the object. Note that these graphs are determined by analysis using the optical analysis software ZEMAX manufactured by ZEMAX Development Corporation. As shown in FIG. 5, when the optical axis of the intraocular lens is aligned with the optical axis of the eyeball optical system in the eye, the intraocular lens employing the reference power distribution 1 provides the best contrast, followed by the intraocular lens according to the present Embodiment 1, and the spherical intraocular lens provides the worst contrast of these lenses.

On the contrary, FIG. 6 is a graph showing the contrasts when the spatial frequency f is 50 lines/mm, in the cases where the intraocular lens according to the Embodiment 1 of the present invention, the spherical intraocular lens, and the intraocular lens employing the reference power distribution 1 are respectively placed, with each optical axis thereof being decentred by 0.5 mm with respect to the optical axis of the intraocular optical system. As shown in FIG. 6, unlike the case where the optical axes are aligned with each other, in the case where the optical axis is decentred, the intraocular lens according to the present embodiment provides the best contrast, followed by the spherical intraocular lens, and the intraocular lens employing the reference power distribution provides the worst.

FIG. 7 is a graph showing the contrasts when the spatial frequency f is 100 lines/mm, in the cases where the intraocular lens according to the Embodiment 1 of the present invention, the spherical intraocular lens, and the intraocular lens employing the reference power distribution are respectively placed, with each optical axis thereof being aligned with the optical axis of the intraocular optical system. FIG. 8 is a graph showing the contrasts when the spatial frequency f is 100 lines/mm, in the cases where the intraocular lens according to the Embodiment 1 of the present invention, the spherical intraocular lens, and the intraocular lens employing the reference power distribution 1 are respectively placed, with each optical axis thereof being decentred by 0.5 mm with respect to the optical axis of the intraocular optical system. As shown in FIGS. 7 and 8, even if the spatial frequency f is increased, as is the case with the above-described cases, it can be seen that the intraocular lens according to the present Embodiment 1 provides the best contrast in the case where the optical axis of the intraocular lens is decentred with respect to the optical axis of the intraocular optical system.

FIG. 9 is a graph showing the relation between the amount of decentration and the contrast when the spatial frequency f is 50 lines/mm, in the cases where the intraocular lens according to the Embodiment 1 of the present invention, the spherical intraocular lens, and the intraocular lens employing the reference power distribution Ma are respectively placed decentred with respect to the optical axis of the intraocular optical system. FIG. 10 is a graph showing the relation between the amount of decentration and the contrast when the spatial frequency f is 100 lines/mm, in the cases where the intraocular lens according to the Embodiment 1 of the present invention, the spherical intraocular lens, and the intraocular lens employing the reference power distribution Ma are respectively placed decentred with respect to the optical axis of the intraocular optical system. As can be seen from these diagrams, the intraocular lens employing the reference power distribution provides a better contrast if the amount of decentration of the intraocular lens is very small, while the intraocular lens according to the embodiment provides a better contrast if the amount of decentration is equal to or more than a certain value, for example, equal to or more than 0.2 to 0.3 mm. Generally speaking, when an intraocular lens is inserted into and placed in the eye, it is common that the lens is decentred by 0.3 mm or more. Eventually, the intraocular lens according to the embodiment provides a better contrast practically. As such, in the case where the lens employing the reference power distribution Ma is inserted into the eye with no decentration, a spot distribution (spot diagram) shows that a point is formed on the optical axis when collimated beam coming from an infinite distance are focused on the image plane, and thus the excellent contrast is provided. In the meantime, in the case where the lens of the Embodiment 1 is inserted into the eye with no decentration, the spot distribution is relatively larger compared with the case of the lens employing the reference power distribution Ma and thus does not form a point, due to existence of the positive power deviation region and the negative power deviation region. However, since the center of the spot distribution is on the optical axis, the amount of power deviation in the deviation region with respect to the reference power distribution Ma is small, and therefore there is no significant difference in contrast.

On the other hand, if the lens is decentred in the eye, the spot distribution is created at a position far from the optical axis with an increased size. In this case, since the lens employing the reference power distribution Ma has the power distribution in which the power decreases along the radial direction, the decentration directly affects the size of the spot distribution, thereby to form a quite large spot distribution. On the contrary, in the case of the lens of the Embodiment 1 ($Mam_1$), the positive power deviation region and the negative power deviation region function in the direction so as to suppress the size of the spot distribution. Accordingly, the lens of the Embodiment 1 ($Mam_1$) forms a smaller size of the spot distribution and provides a higher contrast compared with the lens employing the reference power distribution Ma. This concept can also be applied to lenses with various modes shown in FIGS. 25 and 26 to be described later.

FIG. 11 is a graph showing the power distribution $Mbm_1$ of the intraocular lens according to the Embodiment 2, the power distribution of the spherical intraocular lens, and the reference power distribution Mb. Herein, the reference power distribution curve Mb employs the power distribution in which the powers are the same as those of the spherical intraocular lens in the vicinity of the optical axis, and as to cancel the spherical aberration of the cornea, the powers are decreased with distance closer to the outer periphery. That is, the reference power distribution curve Mb does not employ the power distribution which cancels the spherical aberration of the cornea in the vicinity of the optical axis. In addition, although the reference power distribution curve Mb employs the power distribution so as to cancel the spherical aberration of the cornea in other regions, the power distribution does not perfectly cancel the spherical aberration of the cornea, unlike the reference power distribution Ma.

FIG. 12 is a graph showing the spherical aberrations of the entire eyeball in the cases where the intraocular lens according to the Embodiment 2 of the present invention, the spherical intraocular lens, and the intraocular lens employing the reference power distribution Mb are respectively placed in the eye. In FIG. 12, the curve shown by the solid line represents the aberration distribution curve when the spherical intraocular lens (IOL) is placed, the curve shown by the dotted line in the diagram represents the aberration distribution curve when the intraocular lens employing the reference power distribution Mb is placed, and the curve shown by the dashed-dotted line in the diagram represents the aberration distribution curve when the intraocular lens according to the Embodiment 2 (intraocular lens employing $Mbm_1$) is placed. As shown in FIG. 12, in the Embodiment 2, even in the case of the intraocular lens employing the reference power distribution Mb, the aberration of the cornea is not perfectly corrected, and thus the aberration is not perfectly reduced to zero.

FIG. 13 is a graph showing the contrasts when the spatial frequency f is 50 lines/mm, in the cases where the intraocular lens according to the Embodiment 2 of the present invention, the spherical intraocular lens, and the intraocular lens employing the reference power distribution $M_b$ are respectively placed, with each optical axis thereof being aligned with the optical axis of the intraocular optical system. In the graph of FIG. 13, the vertical axis represents the contrast, and the horizontal axis represents the distance from the object. Note that these graphs are determined by analysis using the optical analysis software ZEMAX manufactured by ZEMAX Development Corporation. As shown in FIG. 13, in the case where the optical axis of the intraocular lens is aligned with the optical axis of the intraocular optical system, the intraocular lens employing the reference power distribution $M_b$ provides the best contrast, followed by the intraocular lens according to the present Embodiment 2 (intraocular lens employing the power distribution $Mbm_1$), and the spherical intraocular lens (spherical IOL) provides the worst contrast of these lens.

On the contrary, FIG. 14 is a graph showing the contrasts when the spatial frequency f is 50 lines/mm, in the cases where the intraocular lens according to the Embodiment 2 of the present invention, the spherical intraocular lens, and the intraocular lens employing the reference power distribution Mb are respectively placed, with each optical axis thereof being decentred by 0.5 mm with respect to the optical axis of the intraocular optical system. As shown in FIG. 14, unlike the case where the optical axes are aligned with each other, in the case where the optical axis is decentred, the intraocular lens according to the present Embodiment 2 provides the best contrast, followed by the spherical intraocular lens, and the intraocular lens employing the reference power distribution Mb provides the worst.

FIG. 15 is a graph showing the contrasts when the spatial frequency f is 100 lines/mm, in the cases where the intraocular lens according to the Embodiment 2 of the present invention, the spherical intraocular lens, and the intraocular lens employing the reference power distribution 2 are respectively placed, with each optical axis thereof being aligned with the optical axis of the intraocular optical system. FIG. 16 is a graph showing the contrasts when the spatial frequency f is 100 lines/mm, in the cases where the intraocular lens according to the Embodiment 2 of the present invention, the spherical intraocular lens, and the intraocular lens employing the reference power distribution Mb are respectively placed, with each optical axis thereof being decentred by 0.5 mm with respect to the optical axis of the intraocular optical system. As shown in FIGS. 15 and 16, even if the spatial frequency f is increased, as is the case with the above-described cases, it can be seen that the intraocular lens according to the present embodiment provides the best contrast, in the case where the optical axis of the intraocular lens is decentred with respect to the optical axis of the intraocular optical system. Note that the relation between the amount of decentration and the contrast when the spatial frequency f is 50 lines/mm, in the cases where the intraocular lens according to the Embodiment 2 (intraocular lens employing the power distribution $Mbm_1$), the spherical intraocular lens, and the intraocular lens employing the reference power distribution Mb are respectively placed decentred with respect to the optical axis of the intraocular optical system is shown in FIG. 27.

FIG. 17 is a graph showing the power distribution of the spherical intraocular lens as a comparative example, the reference power distribution Ma, and the reference power distribution Mb. Herein, the reference power distribution Ma represents the power distribution which perfectly cancels the spherical aberration of the cornea. In the reference power distribution Mb, the powers are the same as those of the spherical intraocular lens in the vicinity of the optical axis, and as to cancel the spherical aberration of the cornea, the powers are decreased with distance closer to the outer periphery. That is, the reference power distribution Mb does not employ the power distribution which cancels the spherical aberration of the cornea in the vicinity of the optical axis. In addition, although the power distribution in other regions is canceling the spherical aberration of the cornea, it does not perfectly cancel the spherical aberration of the cornea, unlike the reference power distribution Ma.

FIG. 18 is a graph showing the spherical aberrations of the entire eyeball, in the cases where the spherical intraocular lens as a comparative example, and the intraocular lenses employing the reference power distribution Ma and the reference power distribution Mb are respectively placed in the eye. In FIG. 18, the curve shown by the solid line represents the aberration distribution curve when the spherical intraocular lens is placed, the curve shown by the dotted line in the diagram represents the aberration distribution curve when the intraocular lens employing the reference power distribution Ma is placed, and the curve shown by the dashed-dotted line in the diagram represents the aberration distribution curve when the intraocular lens employing the reference power distribution Mb is placed. As shown in FIG. 18, the aberration is reduced to zero only in the case of the intraocular lens employing the reference power distribution Ma, and the aberration remains a little in the case of the intraocular lens employing the reference power distribution Mb. In the case of the spherical intraocular lens, the aberration extremely increases with distance closer to the outer periphery of the lens.

FIG. 19 is a graph showing the contrasts when the spatial frequency f is 50 lines/mm, in the cases where the spherical intraocular lens as a comparative example, and the intraocular lens employing the reference power distribution Ma and the reference power distribution Mb are respectively placed, with each optical axis thereof being aligned with the optical axis of the intraocular optical system. In the graph of FIG. 19, the vertical axis represents the contrast, and the horizontal axis represents the distance from the object. Note that these graphs are determined by analysis using the optical analysis software ZEMAX manufactured by ZEMAX Development Corporation. As shown in FIG. 19, it can be seen that, in the case where the optical axis of the intraocular lens is aligned with the optical axis of the intraocular optical system, the intraocular lenses employing the reference power distributions Ma and Mb provide better contrasts compared with the spherical intraocular lens.

On the other hand, FIG. 20 is a graph showing the contrasts when the spatial frequency f is 50 lines/mm, in the cases where the spherical intraocular lens, and the intraocular lenses employing the reference power distributions Ma and Mb are respectively placed, with each optical axis thereof being decentred by 0.5 mm with respect to the optical axis of the intraocular optical system. As shown in FIG. 20, unlike the case where the optical axes are aligned with each other, in the case where the optical axis is decentred, it can be seen that the intraocular lenses employing the reference power distributions Ma and Mb provide worse contrasts compared with the spherical intraocular lens.

FIG. 21 is a graph showing the contrasts when the spatial frequency f is 100 lines/mm, in the cases where the spherical intraocular lens as a comparative example, and the intraocular lenses employing the reference power distributions Ma and Mb are respectively placed, with each optical axis thereof being aligned with the optical axis of the intraocular optical system. FIG. 22 is a graph showing the contrasts when the spatial frequency f is 100 lines/mm, in the cases where the spherical intraocular lens as a comparative example, and the intraocular lenses employing the reference power distributions Ma and Mb are respectively placed, with each optical axis thereof being decentred by 0.5 mm with respect to the optical axis of the intraocular optical system. As shown in FIGS. 21 and 22, even if the spatial frequency f is increased, as is the case with the above-described cases, in the case where the optical axis of the intraocular lens is decentred with respect to the optical axis of the intraocular optical system, it can be seen that the intraocular lenses employing the reference power distributions Ma and Mb provide worse contrasts compared with the spherical intraocular lens.

FIG. 23 is a graph showing the relation between the amount of decentration and the contrast when the spatial frequency f is 50 lines/mm, in the cases where the spherical intraocular lens as a comparative example, and the intraocular lenses employing the reference power distributions Ma and Mb are respectively placed decentred with respect to the optical axis of the intraocular optical system. FIG. 24 is a graph showing the relation between the amount of decentration and the contrast when the spatial frequency f is 100 lines/mm, in the cases where the spherical intraocular lens as a comparative example, and the intraocular lenses employing the reference power distributions Ma and Mb are respectively placed decentred with respect to the optical axis of the intraocular optical system. As can be seen from these diagrams, if the amount of decentration is equal to or greater than approximate 0.4 mm, the intraocular lenses employing the reference power distributions provide worse contrasts than the spherical intraocular lens.

FIG. 25 is a diagram of explaining other modes of the reference power distributions, and FIG. 26 is a diagram showing modes of the power distribution of the intraocular lens according to another embodiment of the invention of the present application. In FIG. 25, $M_1$ and $M_2$ refer to the types of power distribution which respectively include, as a concrete example, the reference power distributions Ma and Mb in the Embodiments 1 and 2. Ma refers to the type of power distribution which perfectly cancels the spherical aberration of the cornea. The reference power distribution is not limited to Type $M_1$, and the power distributions may be of Type $M_2$, $M_3$ and $M_4$. Further, the power distribution of the intraocular lens according to the invention of the present application is not limited to the Embodiment 1 ($Mam_1$) or the Embodiment 2 ($Mbm_1$), as long as the power distribution has, in a region in the vicinity of the center of the intraocular lens, at least one positive power deviation region having a larger power than that represented by the reference power distribution and at least one negative power deviation region having a smaller power than that represented by the reference power distribution. For example, the power distribution of the intraocular lens may be one in which one of adjustment patterns of Types $m_2$ to $m_8$ shown in FIG. 26 is added on one of the reference power distributions shown in FIG. 25. The adjustment pattern refers to the pattern of the power distribution to be added on the reference power distribution, in order to obtain an effect of suppressing deterioration in contrast.

Herein, the reference power distribution of Type $M_1$ as described above refers to the type in which the power decreases in the radial direction, when assuming the power at the center of the lens as the base power. This type includes the reference power distribution Ma in the Embodiment 1. The reference power distribution of Type $M_2$ refers to the type in which the power increases in the radial direction, starts decreasing from a certain radius, and thus is smaller than the base intraocular power at the lens end portion, when assuming the power at the center of the lens as the base power. This type includes the reference power distribution Mb of the Embodiment 2. The reference power distribution of Type $M_3$ refers to the type in which the power is substantially equal to the base power until a certain radius, and then the power starts decreasing from a certain radius in the radial direction, when assuming the power at the center of the lens as the base power. The reference power distribution of Type $M_4$ refers to the type in which the power gradually decreases in the radial direction, and then it sharply decreases from a certain radius, when assuming the power at the center of the lens as the base power.

With respect to the adjustment patterns, Type $m_1$ refers to the type in which the positive power deviation region exists in the center circle and the negative power deviation region exists in an annular region surrounding thereof. Type $m_2$ is a modification of Type $m_1$. Type $m_3$ is the type in which the negative power deviation region exists in the center circle, the positive power deviation region exists in an annular region surrounding thereof, and the negative power deviation region exists in another annular region surrounding the annular region. Type $m_4$ and Type $m_5$ are the types, in which the positive power deviation region exists in the center circle and the negative power deviation region exists in a annular region surrounding thereof, and in which the amounts of deviations are constant in specific ranges both in the positive power deviation region and the negative power deviation region. Type $m_6$ is the type in which the positive power deviation region exists in the center circle, the negative power deviation region exists in an annular region surrounding thereof, the positive power deviation region exists in another annular region surrounding the annular region, and the negative power deviation region exists in a further annular region surrounding the another annular region. Type $m_7$ is the type in which the positive power deviation region and the negative power deviation region are reversed from Type $m_3$. Type $m_8$ is the type in which the positive power deviation regions and the negative power deviation regions are reversed from the type $m_6$.

FIG. 28 is a graph showing the relation between the amount of decentration and the contrast when the spatial frequency f is 50 lines/mm, in the cases where the intraocular lens in which the adjustment pattern of Type $m_1$ is added on the reference power distribution of Type $M_3$, the spherical intraocular lens, and the intraocular lens employing the reference power distribution of Type $M_3$ are respectively placed decentred with respect to the optical axis of the intraocular optical system. FIG. 29 is a graph showing the relation between the amount of decentration and the contrast when the spatial frequency f is 50 lines/mm, in the cases where the intraocular lens in which the adjustment pattern of Type $m_1$ is added on the reference power distribution of Type $M_4$, the spherical intraocular lens, and the intraocular lens employing the reference power distribution of Type $M_4$ are respectively placed decentred with respect to the optical axis of the intraocular optical system. FIG. 30 is a graph showing the relation between the amount of decentration and the contrast when the spatial frequency f is 50 lines/mm, in the cases where the intraocular lens in which the adjustment pattern of Type $m_4$ is added on the reference power distribution of Type $M_1$, the spherical intraocular lens, and the intraocular lens employing the reference power distribution of Type $M_1$ are respectively placed decentred with respect to the optical axis of the intraocular optical system. FIG. 31 is a graph showing the relation between the amount of decentration and the contrast when the spatial frequency f is 50 lines/mm, in the cases where the intraocular lens in which the adjustment pattern of Type $m_6$ is added on the reference power distribution of Type $M_1$, the spherical intraocular lens, and the intraocular lens employing the reference power distribution of Type $M_1$ are respectively placed decentred with respect to the optical axis of the intraocular optical system. FIG. 32 is a graph showing the relation between the amount of decentration and the contrast when the spatial frequency f is 50 lines/mm, in the cases where the intraocular lens in which the adjustment pattern of Type $m_3$ is added on the reference power distribution of Type $M_1$, the spherical intraocular lens, and the intraocular lens employing the reference power distribution of Type $M_1$ are respectively placed decentred with respect to the optical axis of the intraocular optical system. As shown in these diagrams, it can be seen that the intraocular lens employing power distribution of any type shown in these diagrams can suppress deterioration in contrast caused by optic decentration. Note that the intraocular lens according to the invention of the present application includes all lenses that are inserted in the eye.

INDUSTRIAL AVAILABILITY

The present invention may also be utilized for an intraocular lens inserted into an anterior chamber of an eyeball after removing the crystalline lens due to cataract or the like, let alone for an intraocular lens inserted into the posterior chamber thereof, an intraocular lens to be used for a phakic eye, or the like.

DESCRIPTION OF NUMERAL

Figure 1:
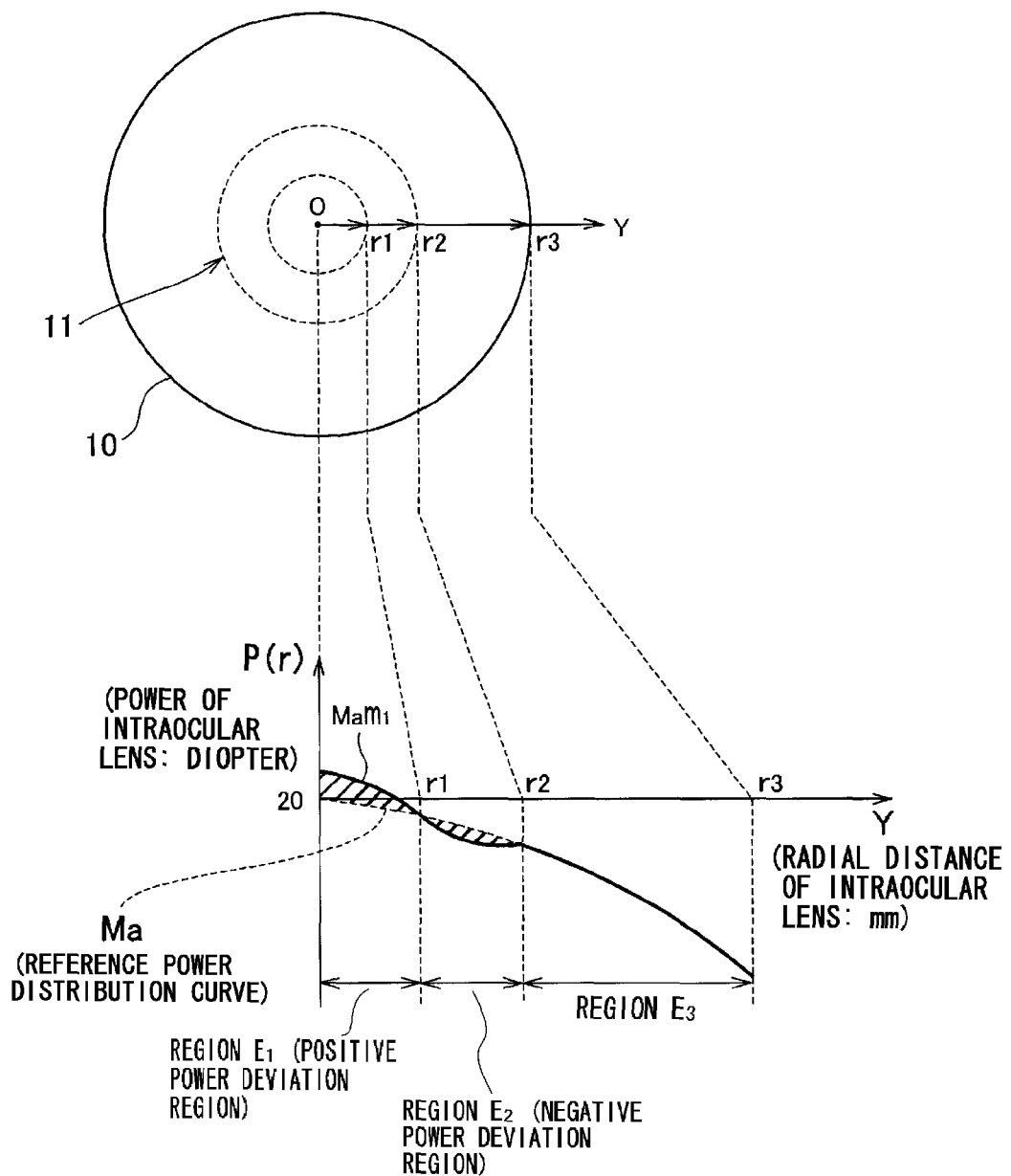
FIG. 1 is an explanatory view of a power distribution of an intraocular lens according to an Embodiment 1 of the present invention.
Figure 2:
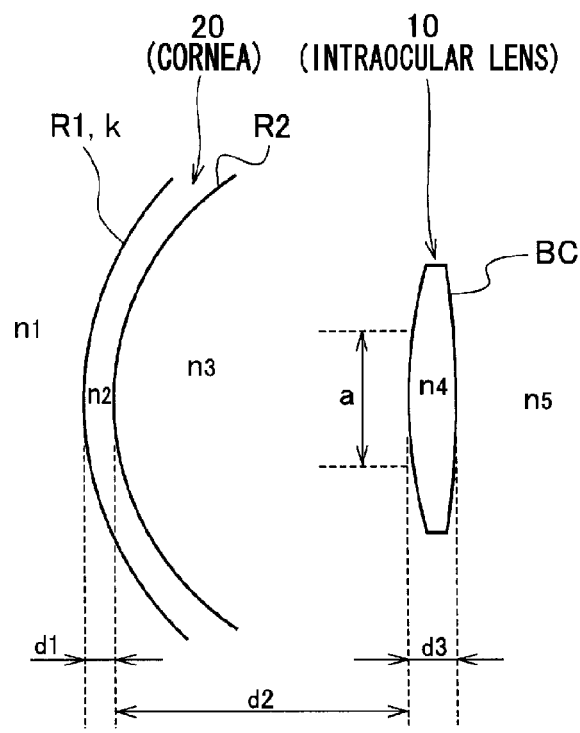
FIG. 2 is a schematic explanatory view of an intraocular optical system constituted by the intraocular lens and cornea.
Figure 3:
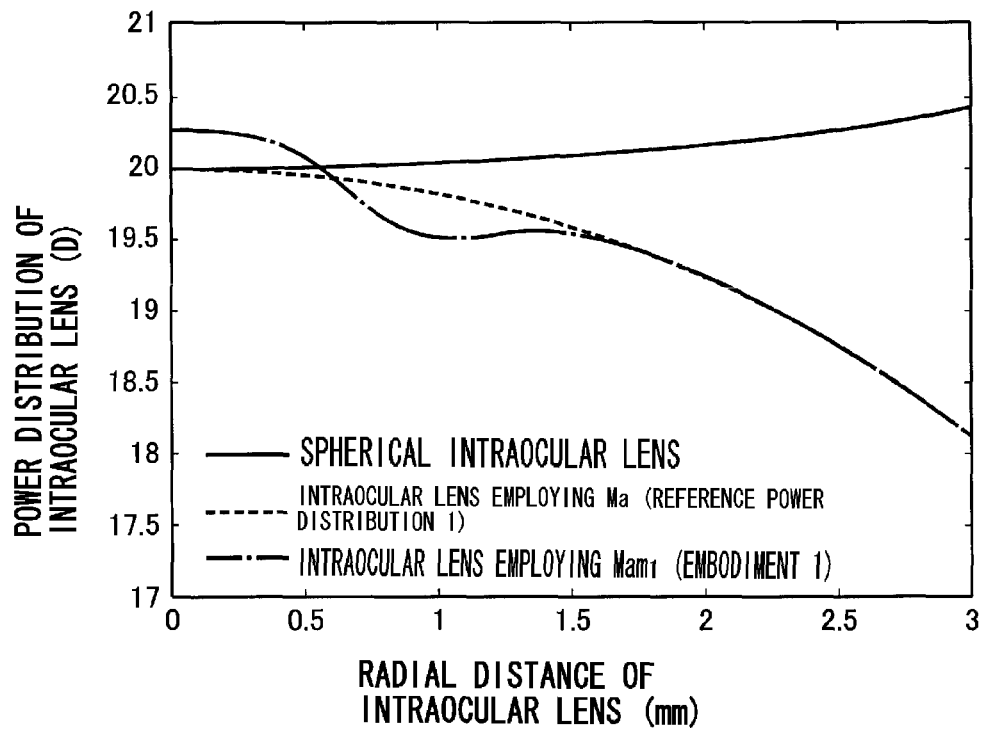
FIG. 3 is a graph showing the power distribution ($Mam_1$) of the intraocular lens according to the Embodiment 1 of the present invention, the power distribution of the spherical intraocular lens, and the reference power distribution Ma.
Figure 4:
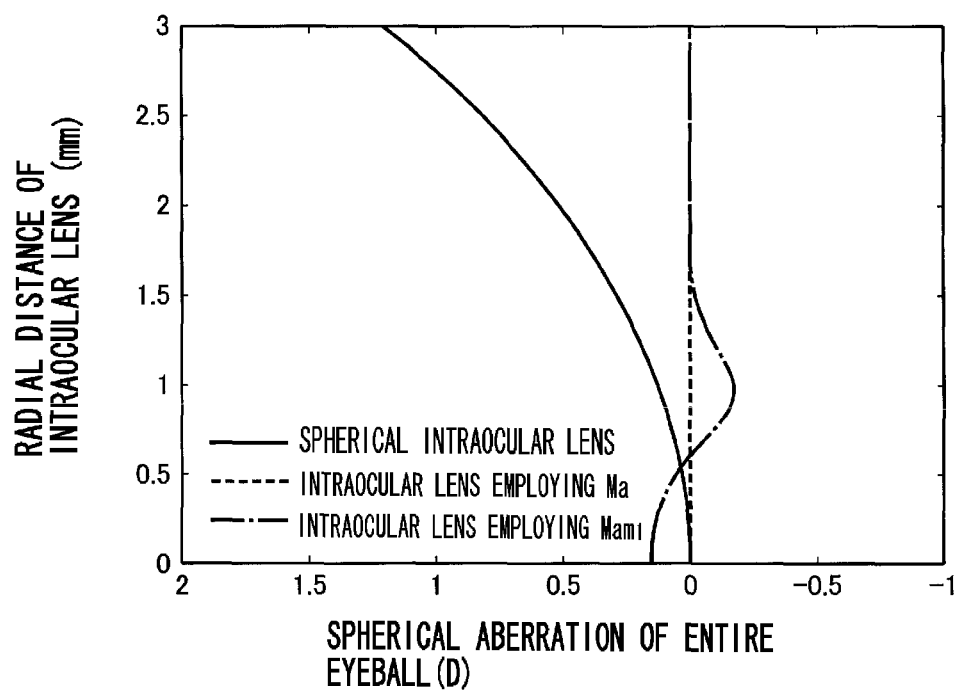
FIG. 4 is a graph showing the spherical aberrations of the entire eyeball, in the cases where the intraocular lens according to the Embodiment 1 of the present invention ($Mam_1$), the spherical intraocular lens, and the intraocular lens employing the reference power distribution Ma are respectively placed in the eye.
Figure 5:
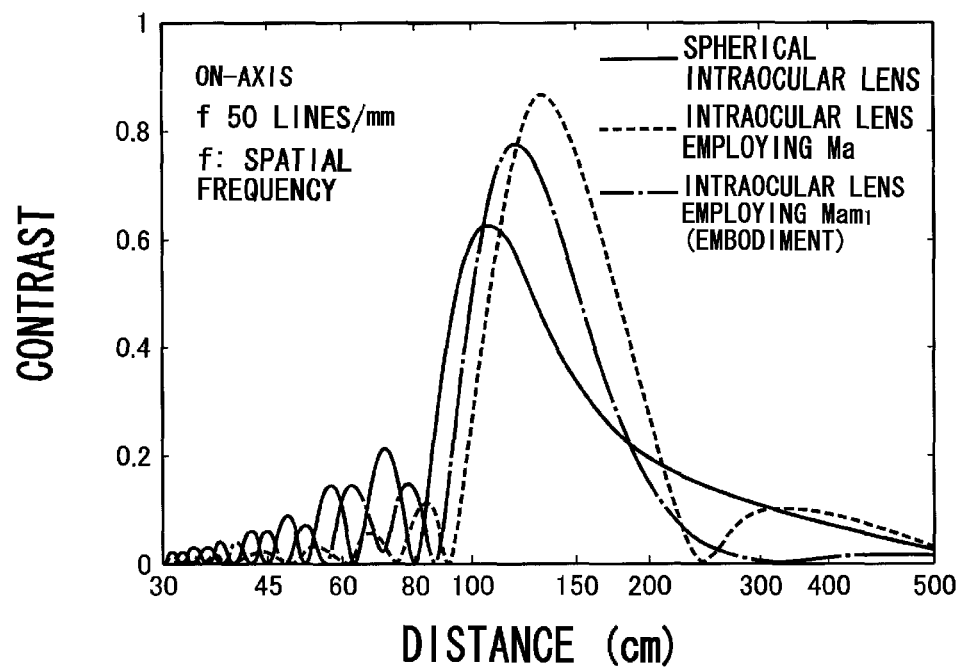
FIG. 5 is a graph showing the contrasts when the spatial frequency f is 50 lines mm, in the cases where the intraocular lens according to the Embodiment 1 of the present invention ($Mam_1$), the spherical intraocular lens, and the intraocular lens employing the reference power distribution Ma are respectively placed, with each optical axis thereof being aligned with the optical axis of the intraocular optical system.
Figure 6:
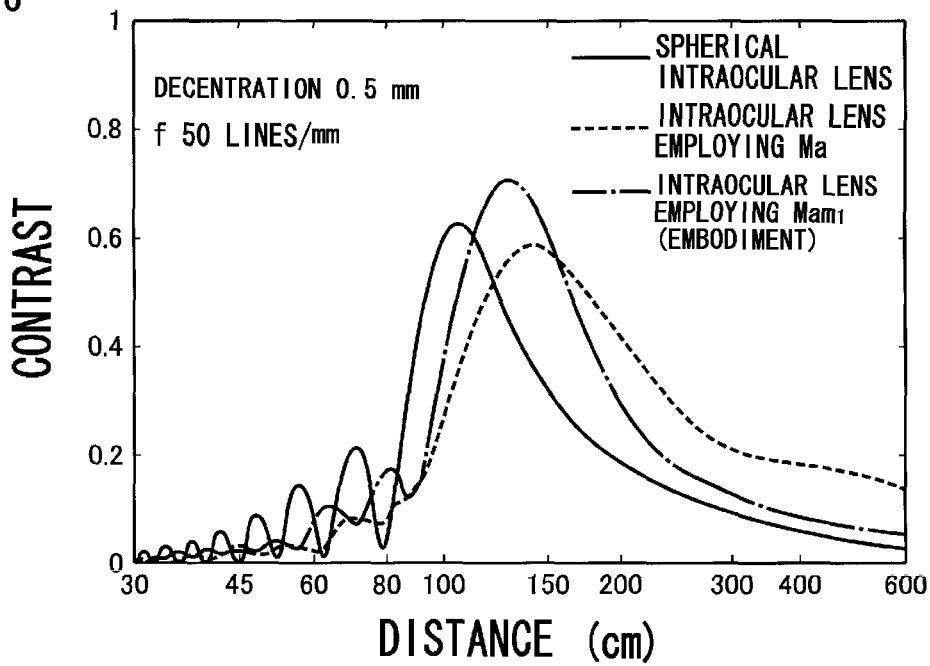
FIG. 6 is a graph showing the contrasts when the spatial frequency f is 50 lines mm, in the cases where the intraocular lens according to the Embodiment 1 of the present invention ($Mam_1$), the spherical intraocular lens, and the intraocular lens employing the reference power distribution Ma are respectively placed, with each optical axis thereof being decentred by 0.5 mm with respect to the optical axis of the intraocular optical system.
Figure 7:
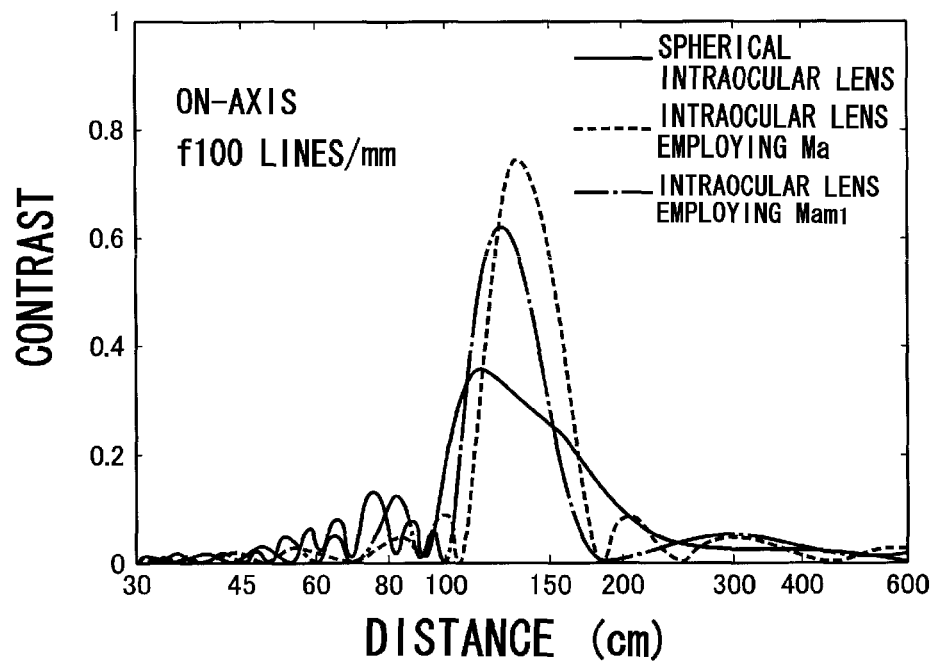
FIG. 7 is a graph showing the contrasts when the spatial frequency f is 100 lines/mm, in the cases where the intraocular lens according to the Embodiment 1 of the present invention ($Mam_1$), the spherical intraocular lens, and the intraocular lens employing the reference power distribution Ma are respectively placed, with each optical axis thereof being aligned with the optical axis of the intraocular optical system.
Figure 8:
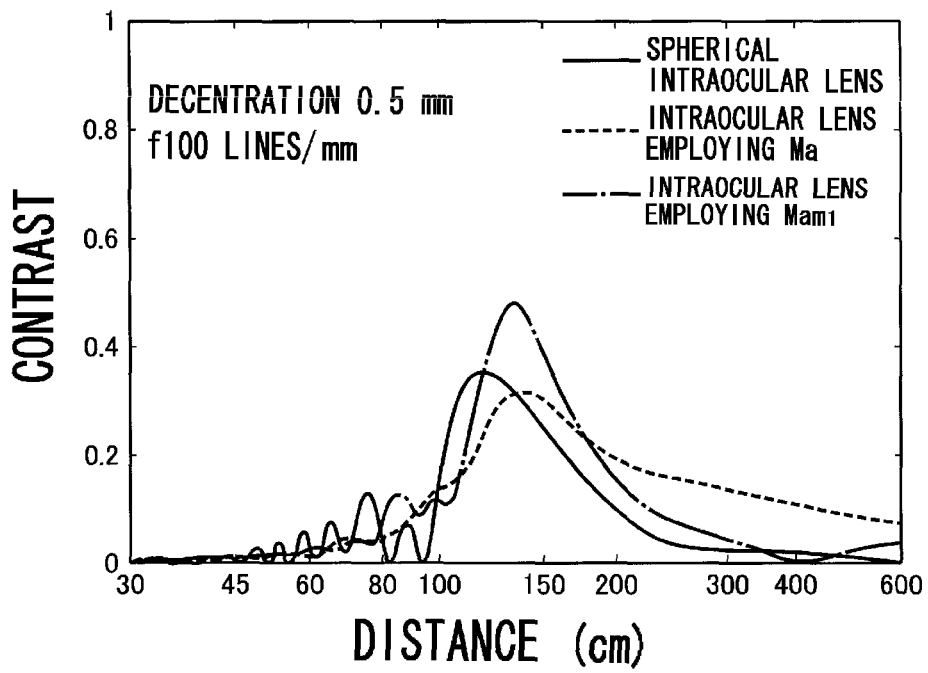
FIG. 8 is a graph showing the contrasts when the spatial frequency f is 100 lines/mm, in the cases where the intraocular lens according to the Embodiment 1 of the present invention ($Mam_1$), the spherical intraocular lens, and the intraocular lens employing the reference power distribution Ma are respectively placed, with each optical axis thereof being decentred by 0.5 mm with respect to the optical axis of the intraocular optical system.
Figure 9:
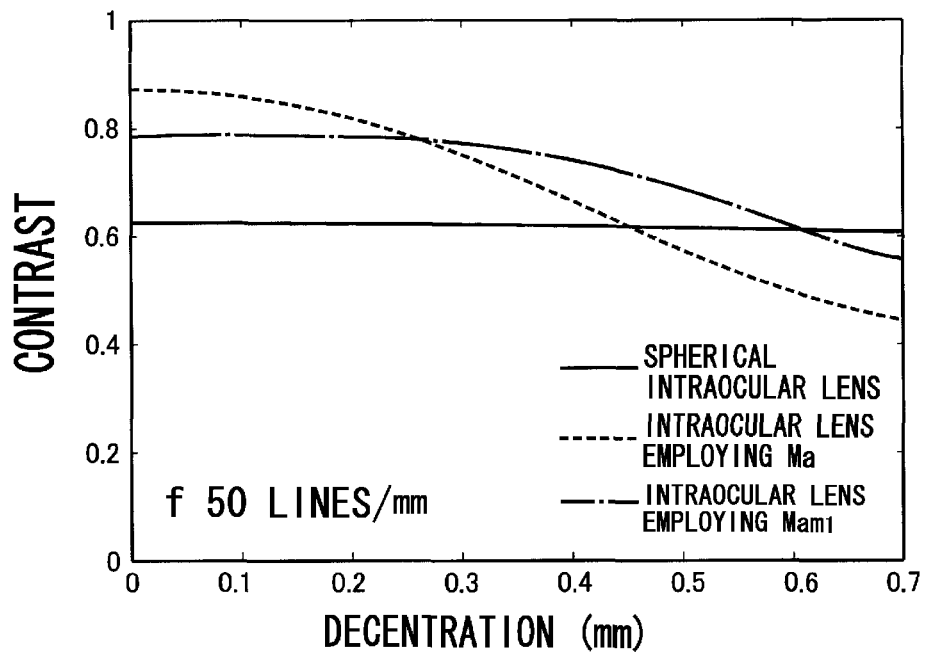
FIG. 9 is a graph showing the relation between the amount of decentration and the contrast when the spatial frequency f is 50 lines/mm, in the cases where the intraocular lens according to the Embodiment 1 of the present invention ($Mam_1$), the spherical intraocular lens, and the intraocular lens employing the reference power distribution Ma are respectively placed decentred with respect to the optical axis of the intraocular optical system.
Figure 10:
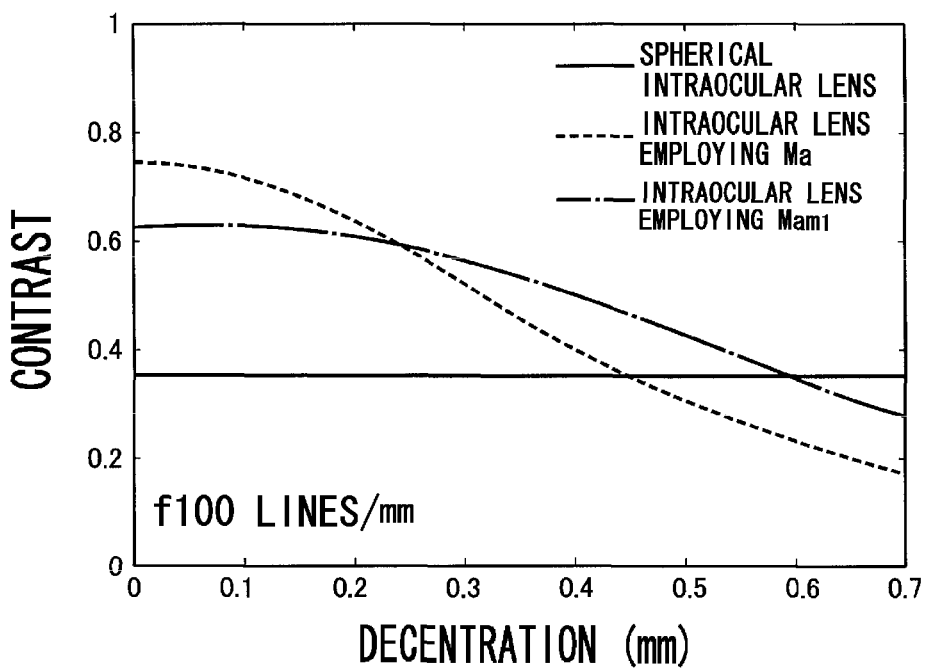
FIG. 10 is a graph showing the relation between the amount of decentration and the contrast when the spatial frequency f is 100 lines/mm, in the cases where the intraocular lens according to the Embodiment 1 of the present invention ($Mam_1$), the spherical intraocular lens, and the intraocular lens employing the reference power distribution Ma are respectively placed decentred with respect to the optical axis of the intraocular optical system.
Figure 11:
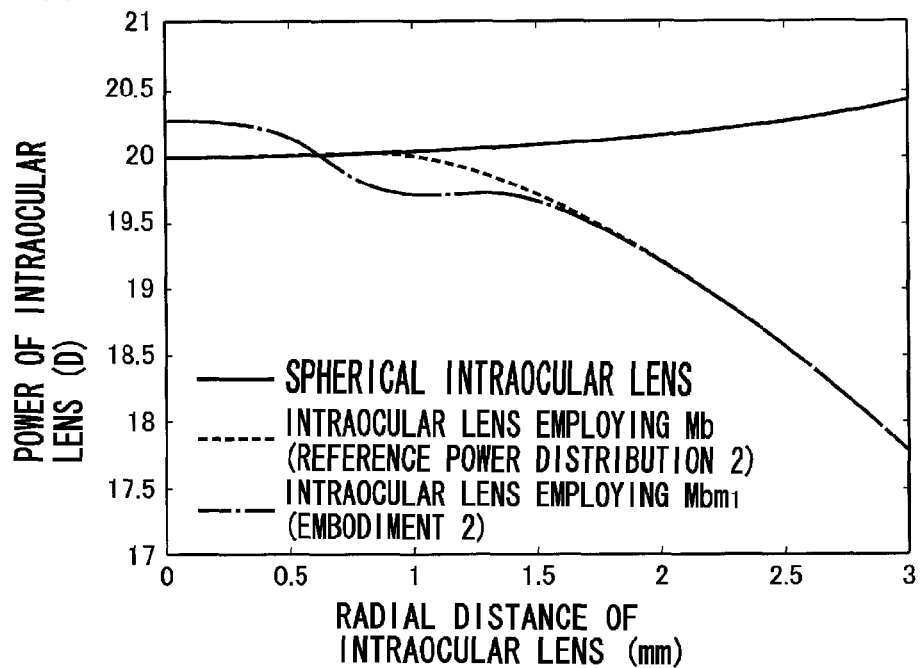
FIG. 11 is the graph showing the power distribution ($Mbm_1$) of the intraocular lens according to the Embodiment 2, the power distribution of the spherical intraocular lens, and the reference power distribution Mb.
Figure 12:
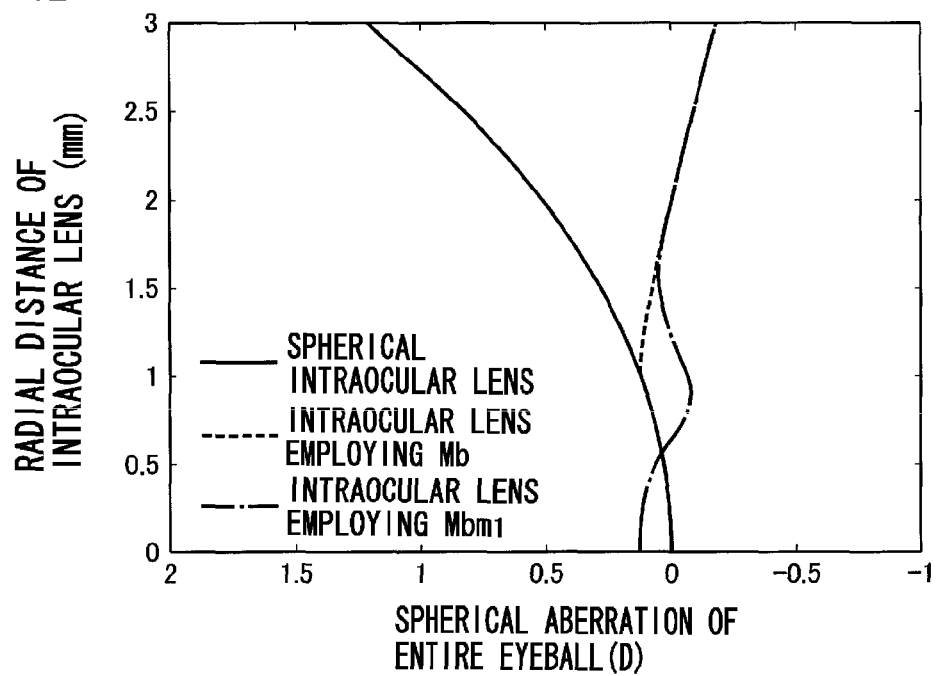
FIG. 12 is a graph showing the spherical aberrations of the entire eyeball, in the cases where the intraocular lens ($Mbm_1$) according to the Embodiment 2 of the present invention, the spherical intraocular lens, and the intraocular lens employing the reference power distribution Mb are respectively placed in the eye.
Figure 13:
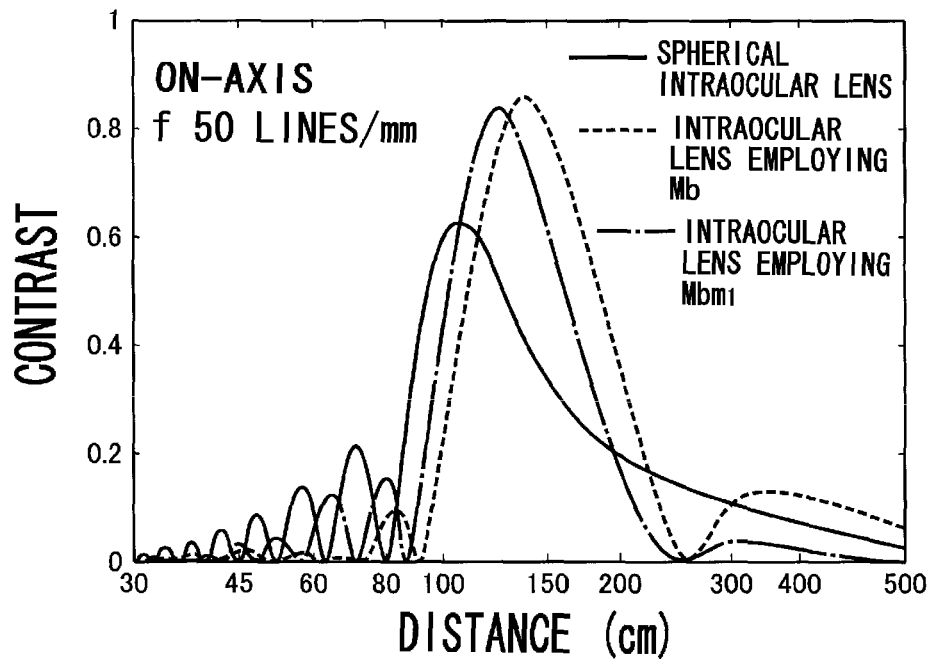
FIG. 13 is a graph showing the contrasts when the spatial frequency f is 50 lines/mm, in the cases where the intraocular lens ($Mbm_1$) according to the Embodiment 2 of the present invention, the spherical intraocular lens, and the intraocular lens employing the reference power distribution Mb are respectively placed, with each optical axis thereof being aligned with the optical axis of the intraocular optical system.
Figure 14:
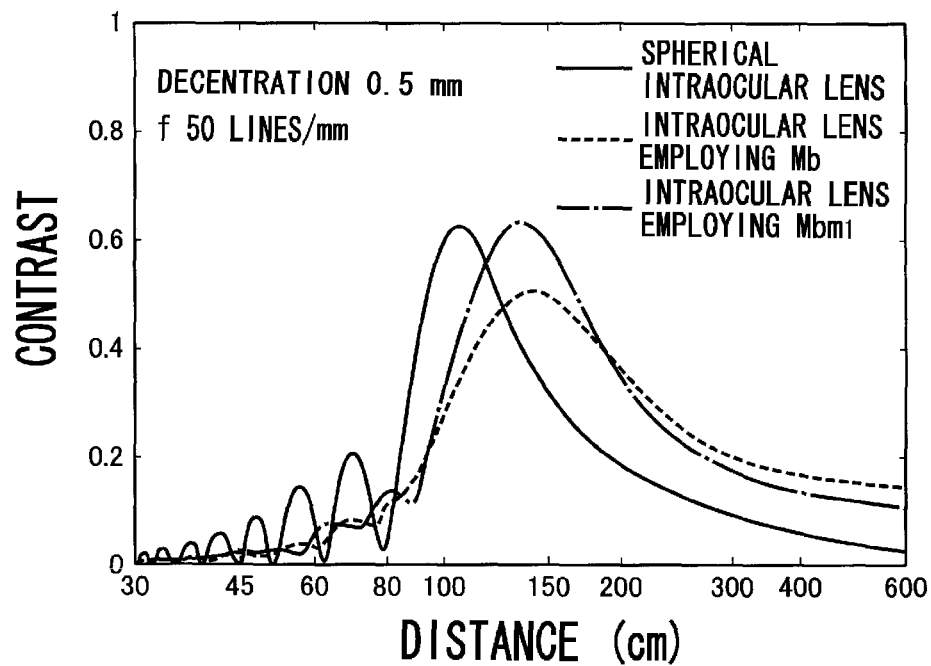
FIG. 14 is a graph showing the contrasts when the spatial frequency f is 50 lines/mm, in the cases where the intraocular lens ($Mbm_1$) according to the Embodiment 2 of the present invention, the spherical intraocular lens, and the intraocular lens employing the reference power distribution Mb are respectively placed, with each optical axis thereof being decentred by 0.5 mm with respect to the optical axis of the intraocular optical system.
Figure 15:
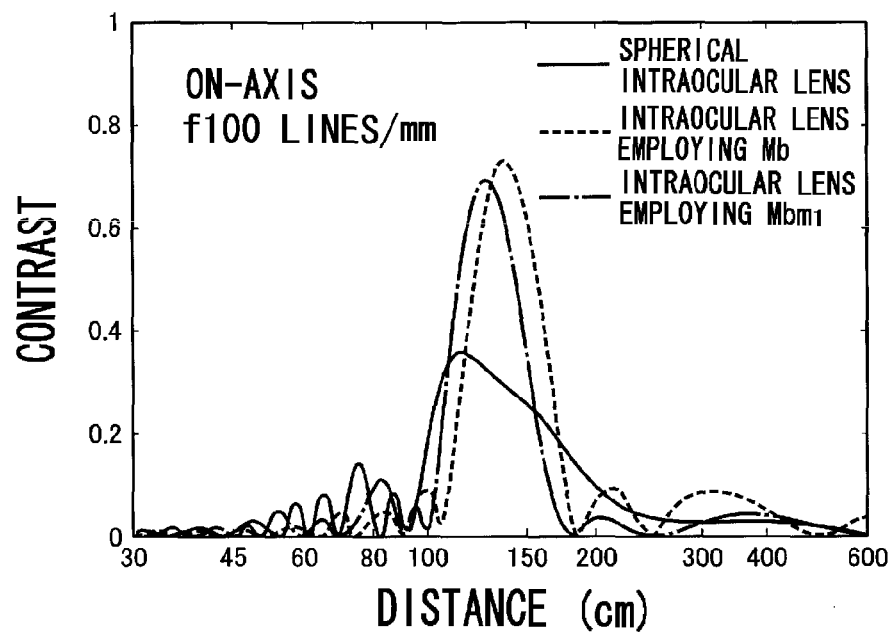
FIG. 15 is a graph showing the contrasts when the spatial frequency f is 100 lines/mm, in the cases where the intraocular lens ($Mbm_1$) according to the Embodiment 2 of the present invention, the spherical intraocular lens, and the intraocular lens employing the reference power distribution Mb are respectively placed, with each optical axis thereof being aligned with the optical axis of the intraocular optical system.
Figure 16:
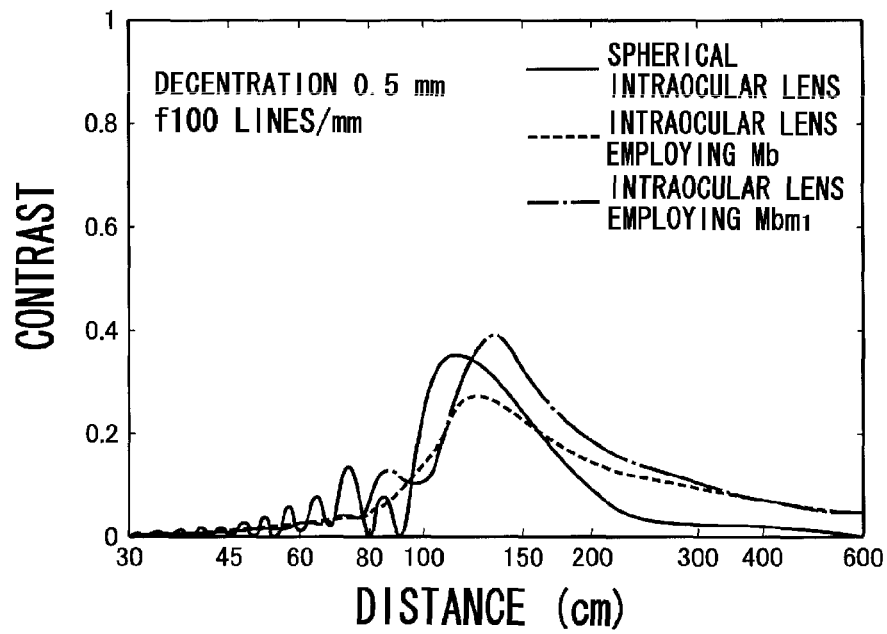
FIG. 16 is a graph showing the contrasts when the spatial frequency f is 100 lines/mm, in the cases where the intraocular lens ($Mbm_1$) according to the Embodiment 2 of the present invention, the spherical intraocular lens, and the intraocular lens employing the reference power distribution Mb are respectively placed, with each optical axis thereof being decentred by 0.5 mm with respect to the optical axis of the intraocular optical system.
Figure 17:
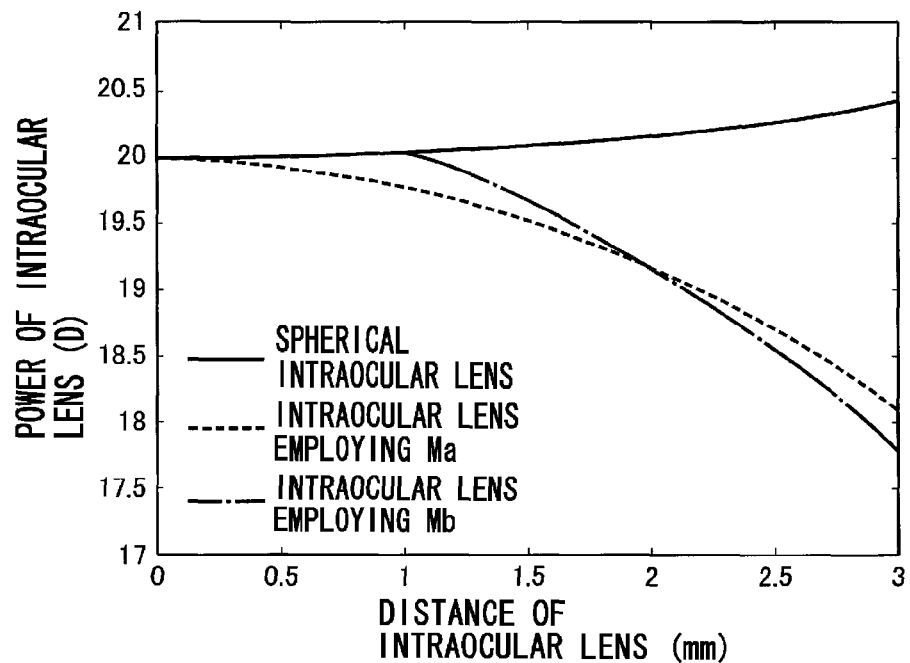
FIG. 17 is a graph showing the power distribution of the spherical intraocular lens as a comparative example, the reference power distribution Ma, and the reference power distribution Mb.
Figure 18:
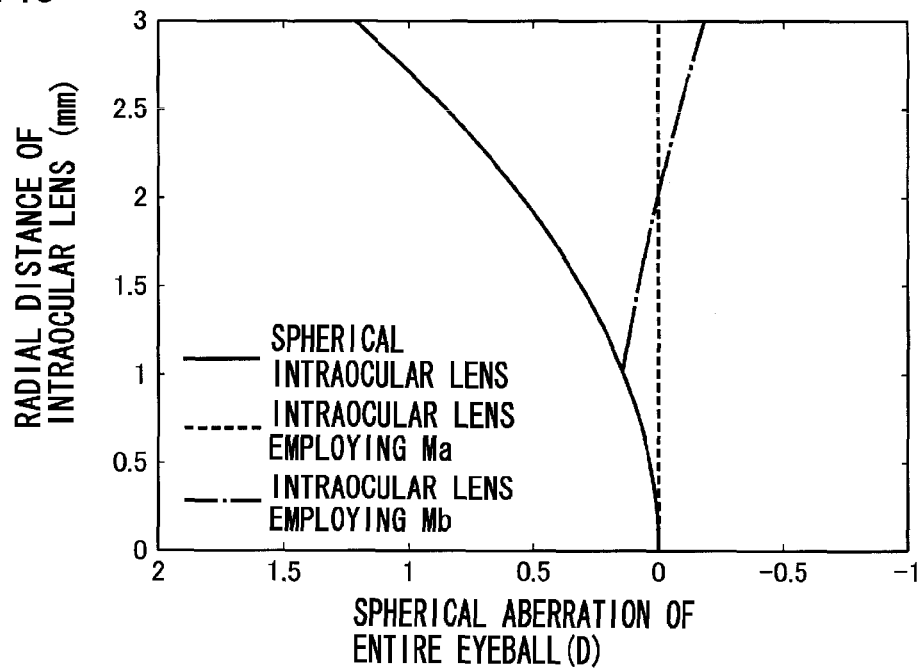
FIG. 18 is a graph showing the spherical aberrations of the entire eyeball in the cases where the spherical intraocular lens as a comparative example, and the lenses employing the reference power distribution Ma and the reference power distribution Mb are respectively placed in the eye.
Figure 19:
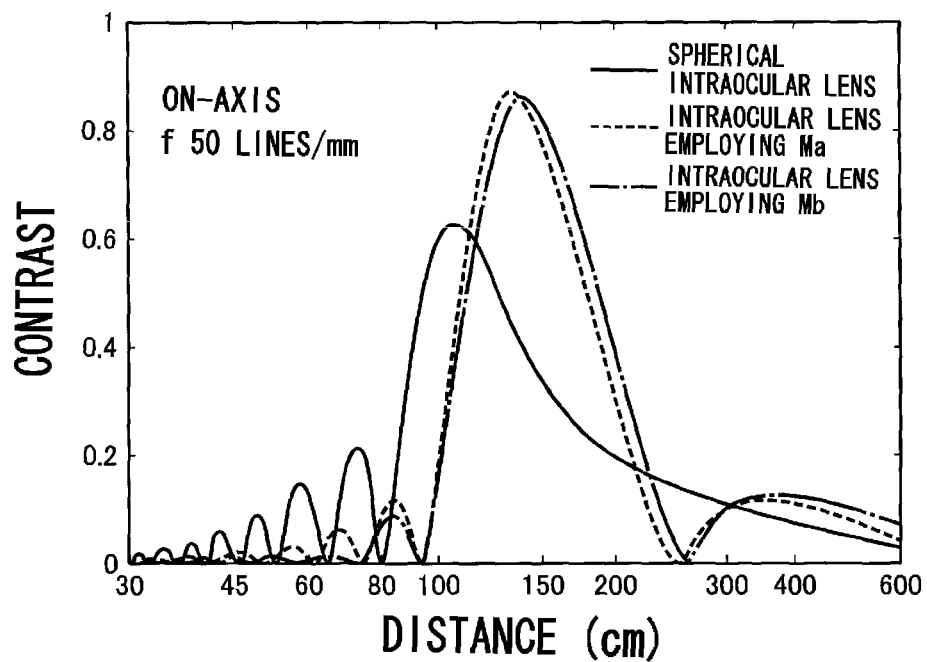
FIG. 19 is a graph showing the contrasts when the spatial frequency f is 50 lines/mm, in the cases where the spherical intraocular lens as a comparative example, and the intraocular lenses employing the reference power distribution Ma and the reference power distribution Mb are respectively placed, with each optical axis thereof being aligned with the optical axis of the intraocular optical system.
Figure 20:
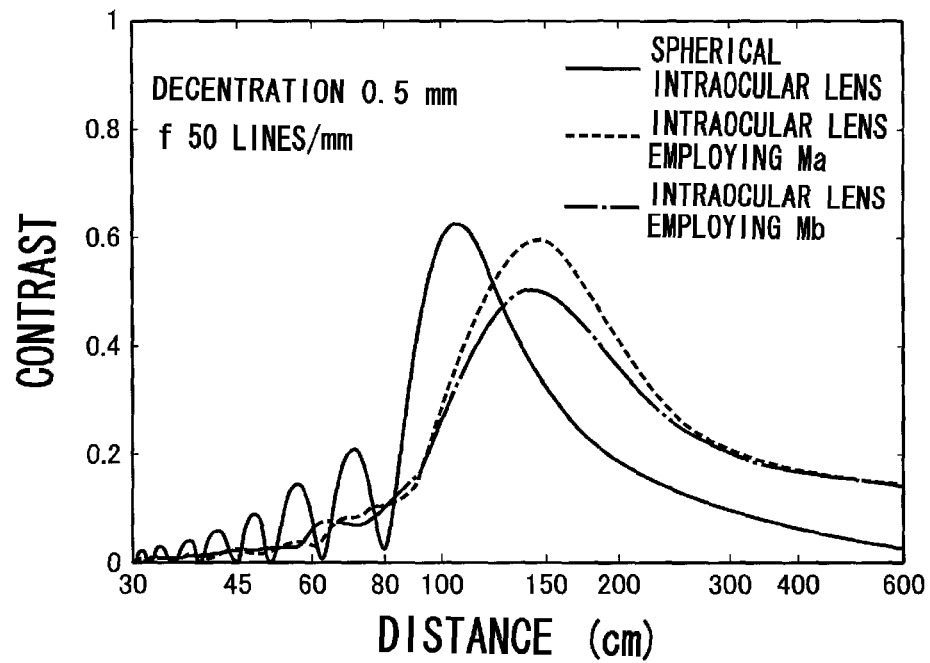
FIG. 20 is a graph showing the contrasts when the spatial frequency f is 50 lines/mm, in the cases where the spherical intraocular lens, and the intraocular lenses employing the reference power distributions Ma and Mb are respectively placed, with each optical axis thereof being decentred by 0.5 mm with respect to the optical axis of the intraocular optical system.
Figure 21:
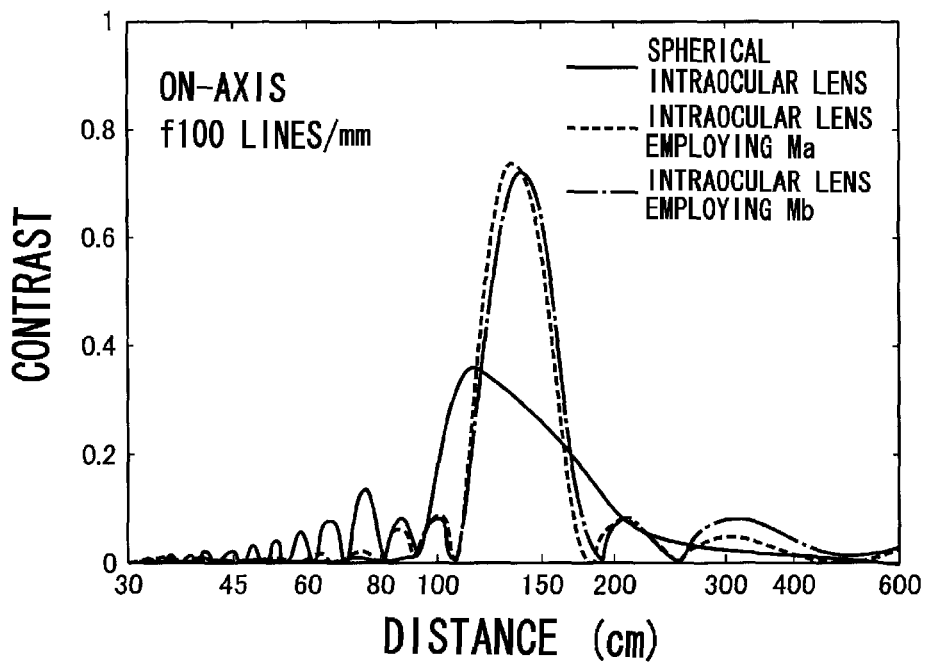
FIG. 21 is a graph showing the contrasts when the spatial frequency f is 100 lines/mm, in the cases where the spherical intraocular lens as a comparative example, and the intraocular lenses employing the reference power distributions Ma and Mb are respectively placed, with each optical axis thereof being aligned with the optical axis of the intraocular optical system.
Figure 22:
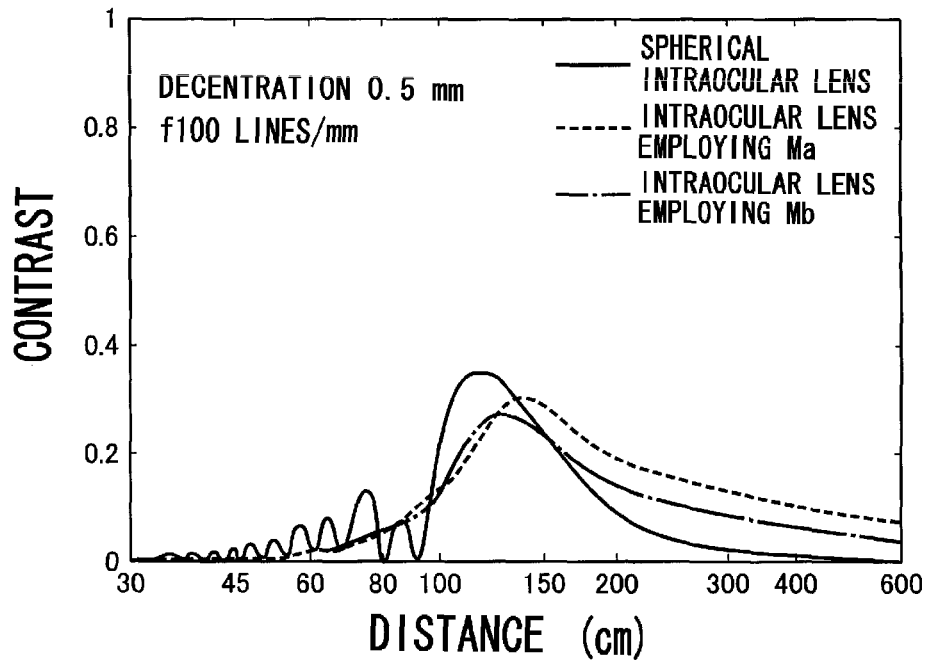
FIG. 22 is a graph showing the contrasts when the spatial frequency f is 100 lines/mm, in the cases where the spherical intraocular lens as a comparative example, and the intraocular lenses employing the reference power distributions Ma and Mb are respectively placed, with each optical axis thereof being decentred by 0.5 mm with respect to the optical axis of the intraocular optical system.
Figure 23:
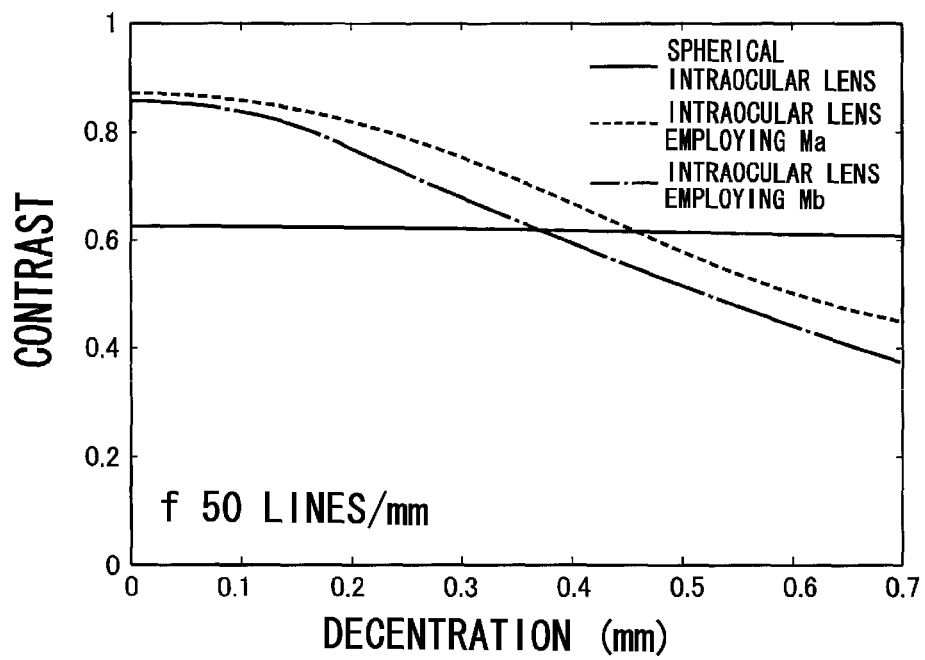
FIG. 23 is a graph showing the relation between the amount of decentration and the contrast when the spatial frequency f is 50 lines/mm, in the cases where the spherical intraocular lens as a comparative example, and the intraocular lenses employing the reference power distributions Ma and Mb are respectively placed decentred with respect to the optical axis of the intraocular optical system.
Figure 24:
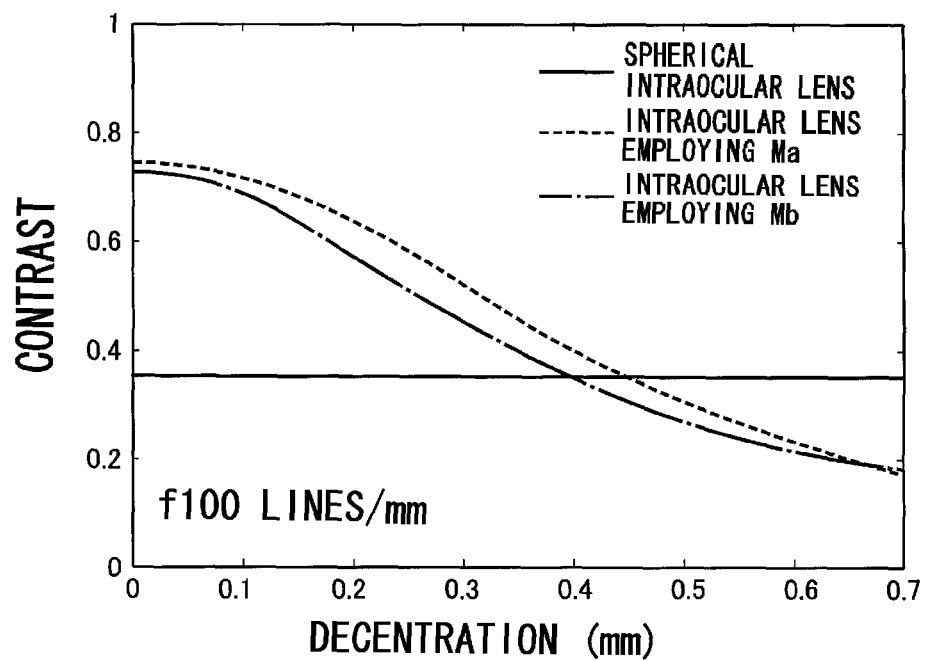
FIG. 24 is a graph showing the relation between the amount of offset and the contrast when the spatial frequency f is 100 lines/mm, in the cases where the spherical intraocular lens as a comparative example, and the intraocular lenses employing the reference power distributions Ma and Mb are respectively placed offset with respect to the optical axis of the intraocular optical system.
Figure 25:
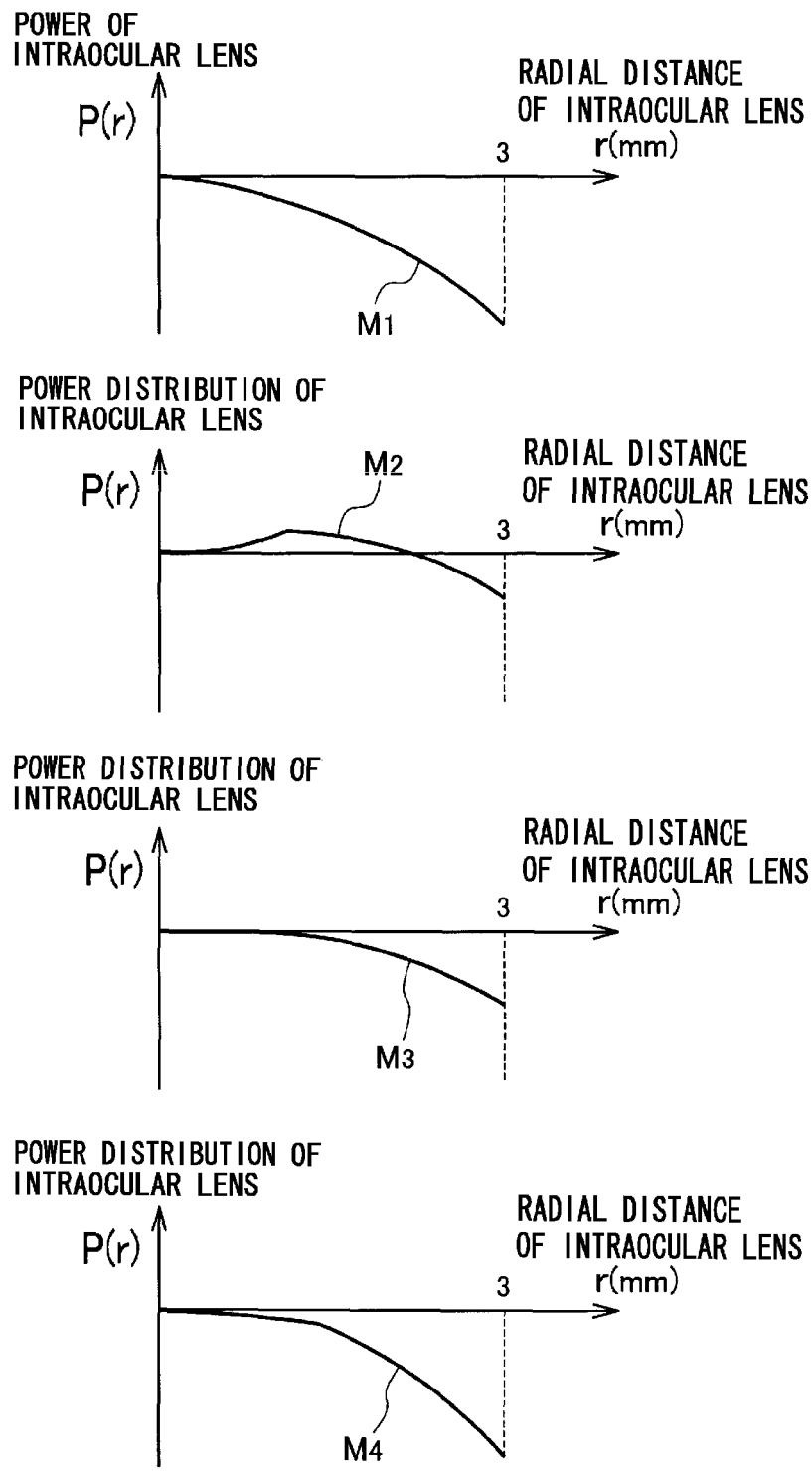
FIG. 25 is a diagram of explaining the modes of the reference power distribution.
Figure 26:
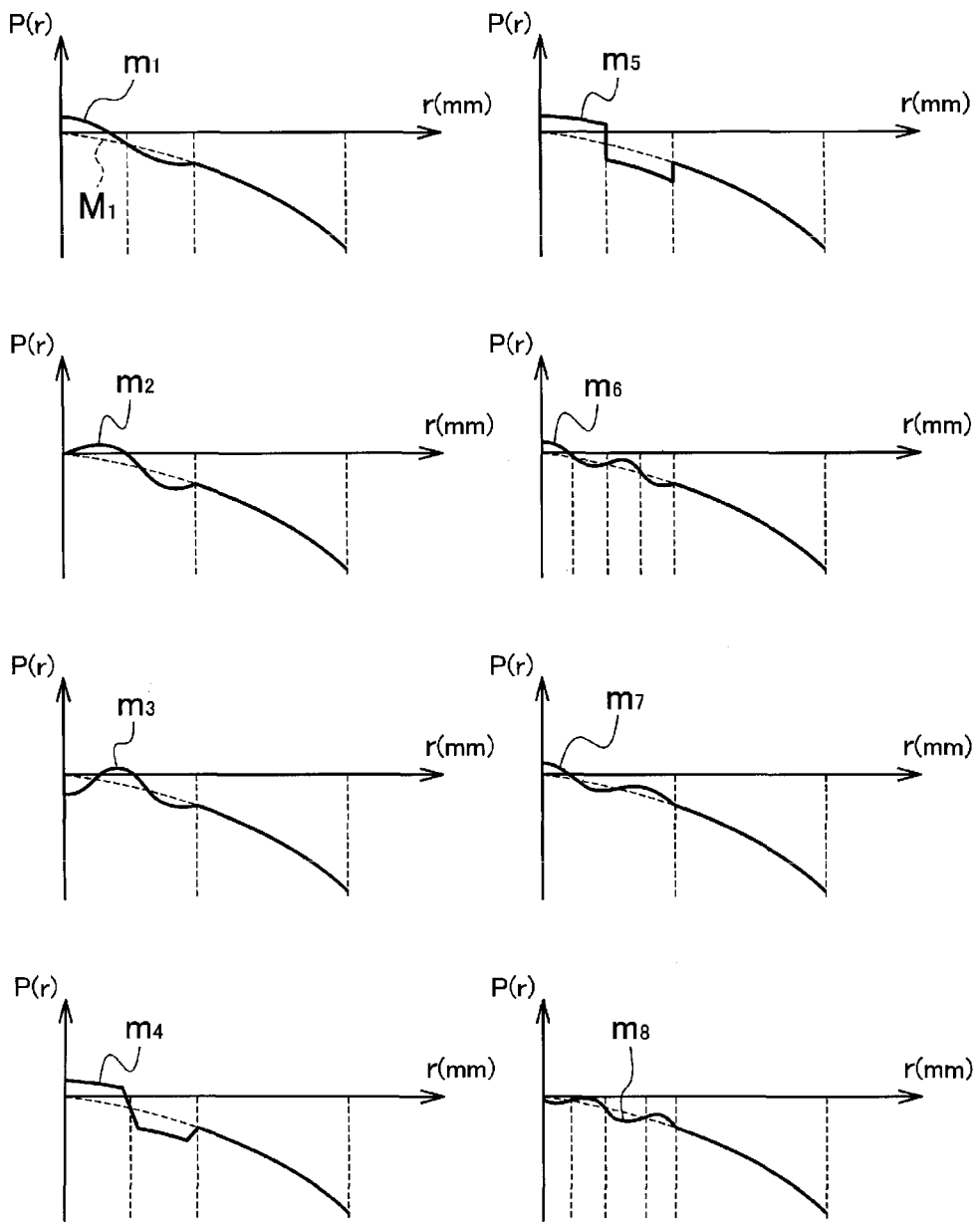
FIG. 26 is a diagram showing the modes of adjustment patterns in the invention of the present application.
Figure 27:
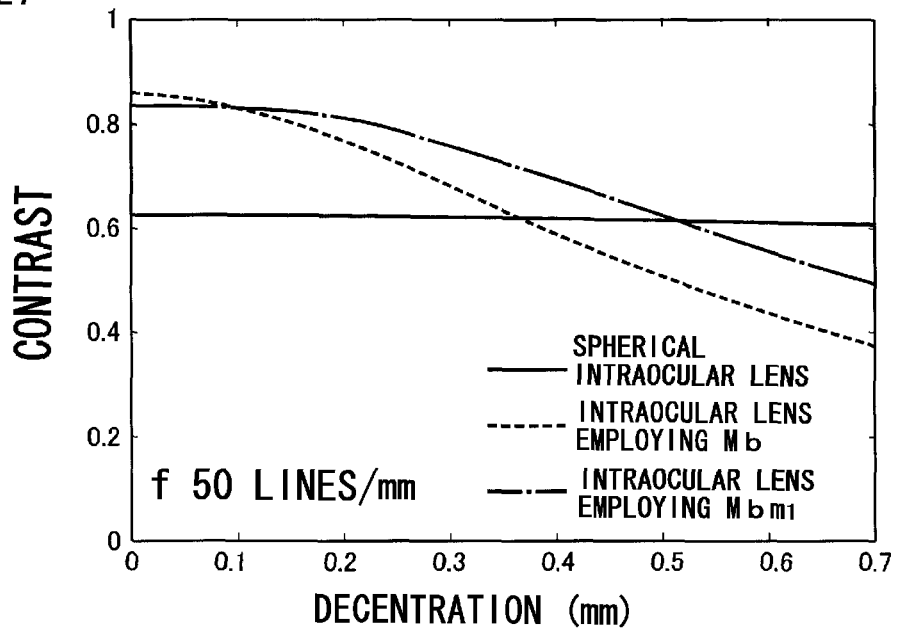
FIG. 27 is a graph showing the relation between the amount of decentration and the contrast when the spatial frequency f is 50 lines/mm, in the cases where the intraocular lens according to the Embodiment 2 of the present invention (intraocular lens employing the power distribution $Mbm_1$), the spherical intraocular lens, and the intraocular lens employing the reference power distribution Mb are respectively placed decentred with respect to the optical axis of the intraocular optical system.
Figure 28:
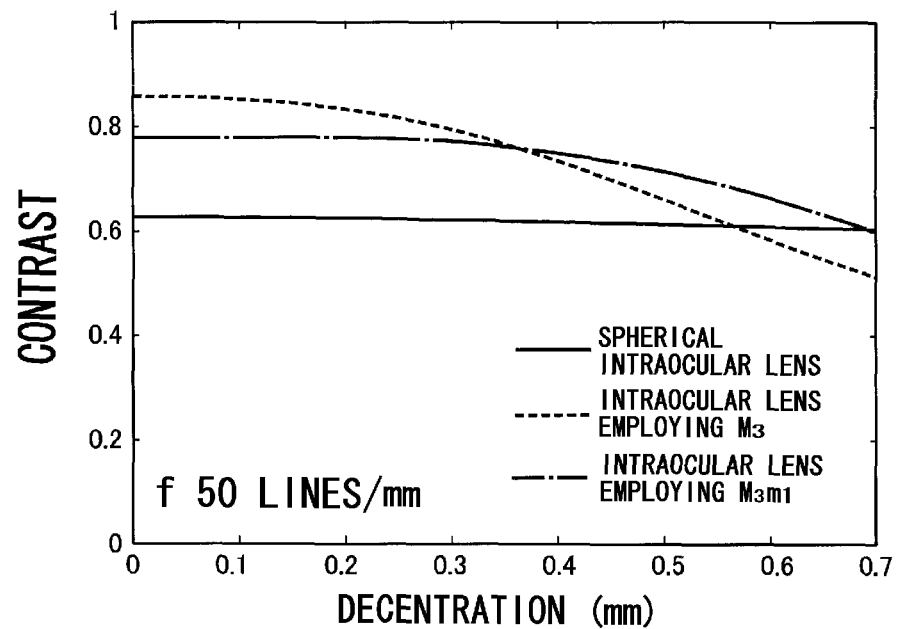
FIG. 28 is a graph showing the relation between the amount of decentration and the contrast when the spatial frequency f is 50 lines/mm, in the cases where the intraocular lens ($M_3m_1$) in which the adjustment pattern of Type $m_1$ is added to the intraocular lens employing the reference power distribution of Type $M_3$, the spherical intraocular lens, and the intraocular lens employing the reference power distribution of Type $M_3$ are respectively placed decentred with respect to the optical axis of the intraocular optical system.
Figure 29:
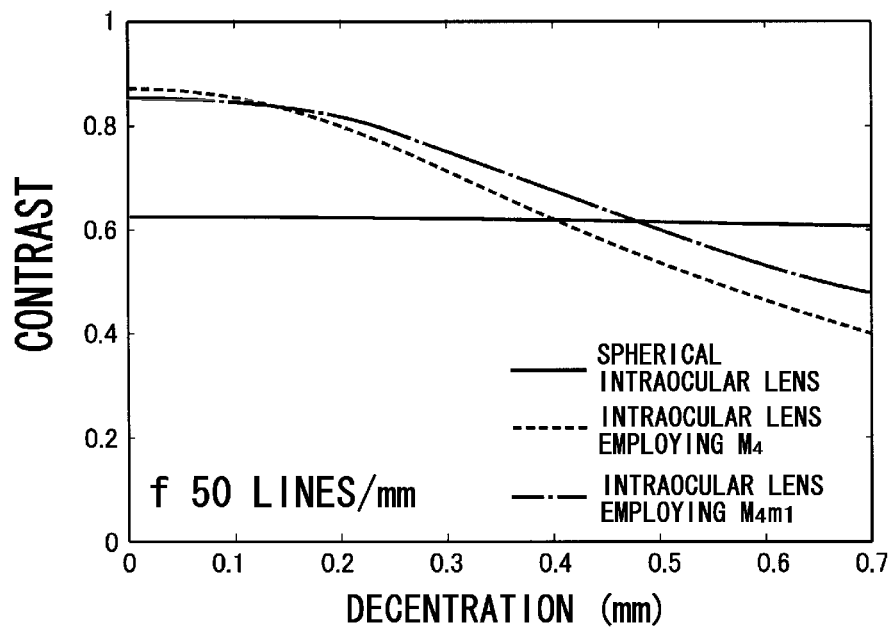
FIG. 29 is a graph showing the relation between the amount of decentration and the contrast when the spatial frequency f is 50 lines/mm, in the cases where the intraocular lens ($M_4m_1$) in which the adjustment pattern of Type $m_1$ is added to the intraocular lens employing the reference power distribution of Type $M_4$, the spherical intraocular lens, and the intraocular lens employing the reference power distribution of Type $M_4$ are respectively placed decentred with respect to the optical axis of the intraocular optical system.
Figure 30:
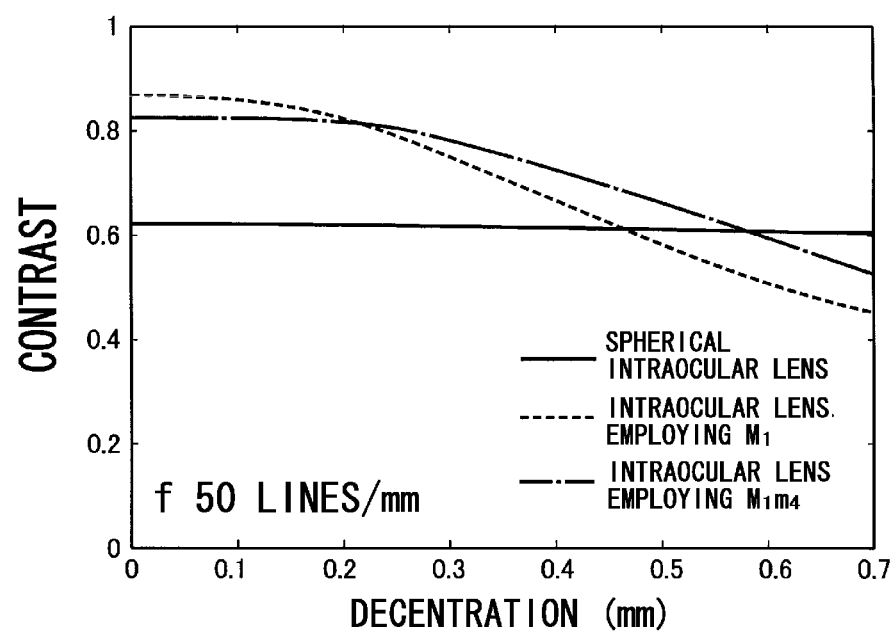
FIG. 30 is a graph showing the relation between the amount of decentration and the contrast when the spatial frequency f is 50 lines/mm, in the cases where the intraocular lens ($M_1m_4$) in which the adjustment pattern of Type $m_5$ is added to the intraocular lens employing the reference power distribution of Type $M_1$, the spherical intraocular lens, and the intraocular lens employing the reference power distribution of Type $M_1$ are respectively placed decentred with respect to the optical axis of the intraocular optical system.
Figure 31:
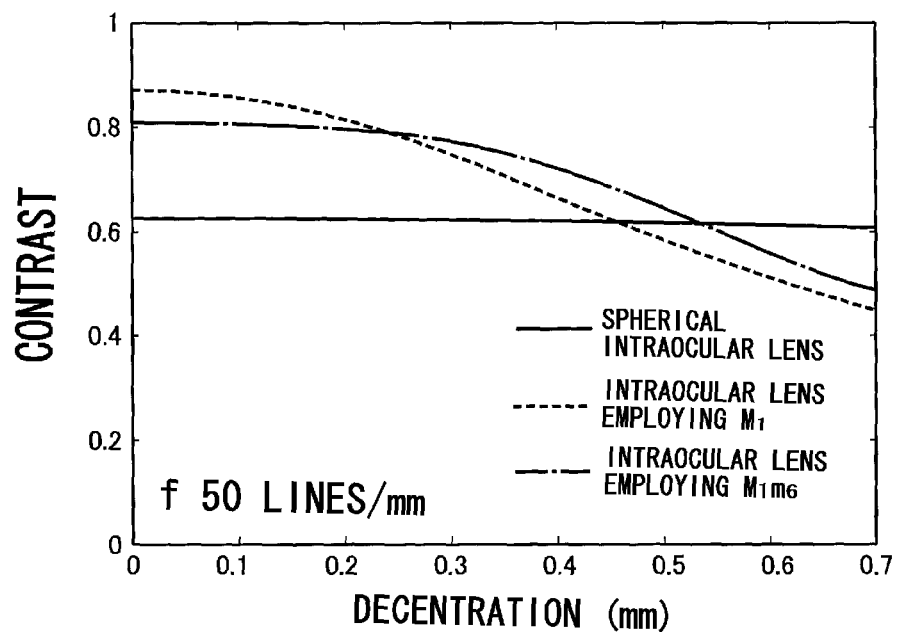
FIG. 31 is a graph showing the relation between the amount of decentration and the contrast when the spatial frequency f is 50 lines/mm, in the cases where the intraocular lens ($M_1m_6$) in which the adjustment pattern of Type $m_6$ is added to the intraocular lens employing the reference power distribution of Type $M_1$, the spherical intraocular lens, and the intraocular lens employing the reference power distribution of Type $M_1$ are respectively placed decentred with respect to the optical axis of the intraocular optical system.
Figure 32:
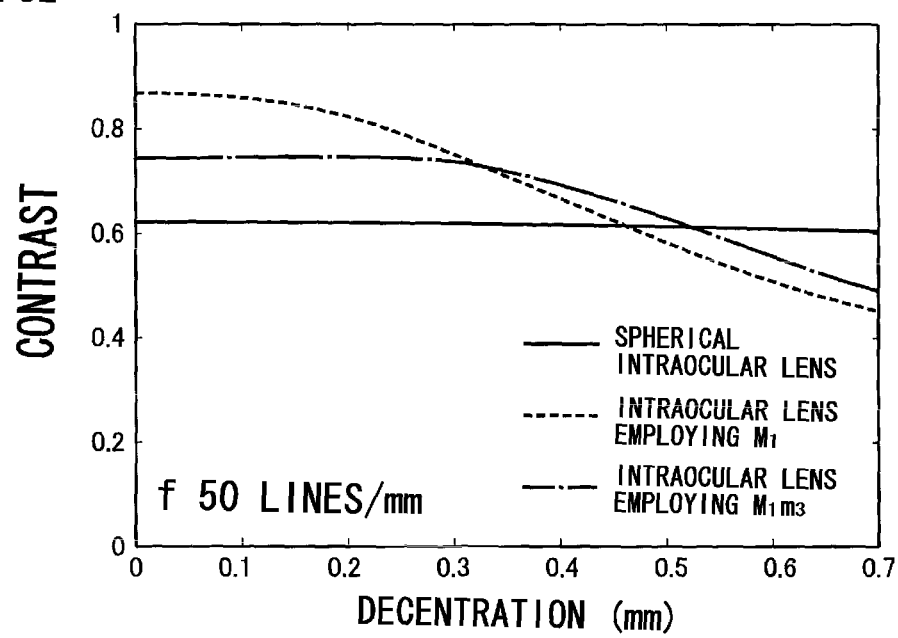
FIG. 32 is a graph showing the relation between the amount of decentration and the contrast when the spatial frequency f is 50 lines/mm, in the cases where the intraocular lens ($M_1m_3$) in which the adjustment pattern of Type $m_3$ is added to the intraocular lens employing the reference power distribution of Type $M_1$, the spherical intraocular lens, and the intraocular lens employing the reference power distribution of Type $M_1$ are respectively placed decentred with respect to the optical axis of the intraocular optical system.
Figure 33:
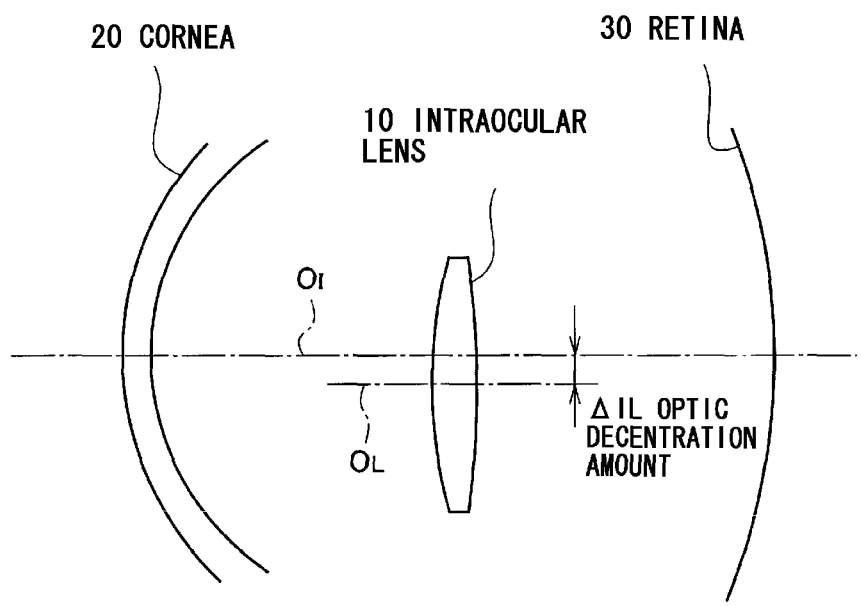
FIG. 33 is a diagram showing that the optical axis of the intraocular lens is decentred from the optical axis of the eyeball.

10 Intraocular lens (IOL)
11 A region in the vicinity of an optical center O
12 Cornea

The invention claimed is:

1. An intraocular lens for use in an eye having an optical axis and a spherical aberration of the cornea, the intraocular lens comprising:
    an optical axis;
    a reference power distribution region defining a power distribution that is equal to a reference power distribution that is set to cancel, but not perfectly cancel, the spherical aberration of the cornea when the intraocular lens is inserted into the eye;
    a positive power deviation region, defining a power distribution that is greater than the reference power distribution, that is radially inward of the reference power distribution region, substantially circular, non-annular, and centered relative to the optical axis, wherein the power of the positive power deviation region is greater than reference power at the optical axis; and
    a negative power deviation region, defining a power distribution that is less than the reference power distribution, that is radially inward of the reference power distribution region, is substantially annular and centered relative to the optical axis.

2. An intraocular lens as claimed in claim 1, wherein the positive power deviation region and the negative power deviation region are located within a central region that defines a substantially circular shape centered around the optical axis and a radius of not less than 0.7 mm and not more than 1.75 mm.

3. An intraocular lens as claimed in claim 1, wherein a mean value of power deviation amounts from the reference power distribution in the positive power deviation region is not less than 0.1 diopter and not more than 0.8 diopter, and a mean value of power deviation amounts from the reference power distribution in the negative power deviation region is not less than 0.1 diopter and not more than 0.8 diopter.

4. An intraocular lens as claimed in claim 1, wherein the positive power deviation region defines an average positive power deviation from the reference power distribution, the negative power deviation region defines an average negative power deviation from the reference power distribution, and the absolute value of the average positive power deviation is equal to the absolute value of the average negative power deviation.

5. An intraocular lens as claimed in claim 1, wherein there is only one positive power deviation region and there is only one negative power deviation region.

6. An intraocular lens as claimed in claim 1, wherein the power deviation of the positive power deviation region is greatest at the optical axis.

7. An intraocular lens as claimed in claim 1, wherein deterioration in contrast is reduced, as compared to an intraocular lens with the same reference power distribution and no positive and negative power deviation regions, when the optical axis of the intraocular lens is de-centered from the optical axis of the eye.

8. An intraocular lens for use in an eye having an optical axis and a spherical aberration of the cornea, the intraocular lens comprising:
an optical axis;
a reference power distribution region defining a power distribution that is equal to a reference power distribution that is set to cancel the spherical aberration of the cornea when the intraocular lens is inserted into the eye;
a negative power deviation region, defining a power distribution that is less than the reference power distribution, that is radially inward of the reference power distribution region, substantially circular, non-annular, centered relative to the optical axis, and that has a power that is less than reference power at the optical axis; and
a positive power deviation region, defining a power distribution that is greater than the reference power distribution, that is radially inward of the reference power distribution region, is substantially annular and centered relative to the optical axis;
wherein there is only one positive power deviation region and there is only one negative power deviation region.

9. An intraocular lens as claimed in claim 8, wherein the positive power deviation region and the negative power deviation region are located within a central region that defines a substantially circular shape centered around the optical axis and a radius of not less than 0.7 mm and not more than 1.75 mm.

10. An intraocular lens as claimed in claim 8, wherein a mean value of power deviation amounts from the reference power distribution in the positive power deviation region is not less than 0.1 diopter and not more than 0.8 diopter, and a mean value of power deviation amounts from the reference power distribution in the negative power deviation region is not less than 0.1 diopter and not more than 0.8 diopter.

11. An intraocular lens as claimed in claim 8, wherein the positive power deviation region defines an average positive power deviation from the reference power distribution, the negative power deviation region defines an average negative power deviation from the reference power distribution, and the absolute value of the average positive power deviation is equal to the absolute value of the average negative power deviation.

12. An intraocular lens as claimed in claim 8, wherein the power deviation of the positive power deviation region is greatest at the optical axis.

13. An intraocular lens as claimed in claim 8, wherein deterioration in contrast is reduced, as compared to an intraocular lens with the same reference power distribution and no positive and negative power deviation regions, when the optical axis of the intraocular lens is de-centered from the optical axis of the eye.

* * * * *